United States Patent
Toy

(10) Patent No.: US 12,232,822 B2
(45) Date of Patent: Feb. 25, 2025

(54) INTRAOPERATIVE ANGLE MEASUREMENT APPARATUS, SYSTEM, AND METHOD

(71) Applicant: Jason Onur Toy, Austin, TX (US)

(72) Inventor: Jason Onur Toy, Austin, TX (US)

(*) Notice: Subject to any disclaimer, the term of this patent is extended or adjusted under 35 U.S.C. 154(b) by 408 days.

(21) Appl. No.: 17/581,939

(22) Filed: Jan. 23, 2022

(65) Prior Publication Data

US 2022/0323156 A1 Oct. 13, 2022

Related U.S. Application Data

(60) Provisional application No. 63/117,176, filed on Nov. 23, 2020.

(51) Int. Cl.
*A61B 34/20* (2016.01)
*A61B 90/00* (2016.01)

(52) U.S. Cl.
CPC .............. *A61B 34/20* (2016.02); *A61B 90/06* (2016.02); *A61B 2034/2051* (2016.02); *A61B 2090/067* (2016.02)

(58) Field of Classification Search
CPC ... A61B 34/20; A61B 90/06; A61B 2090/067; A61B 5/067
See application file for complete search history.

(56) References Cited

U.S. PATENT DOCUMENTS

| | | | |
|---|---|---|---|
| 5,156,162 A | 10/1992 | Gerhardt | |
| 6,050,960 A | 4/2000 | Ferzli | |
| 6,637,278 B1 | 10/2003 | Fasanella | |
| 9,937,062 B2 | 4/2018 | Stein | |
| 9,993,177 B2 | 6/2018 | Chien et al. | |
| 10,524,723 B2 | 1/2020 | Le Huec et al. | |
| 2008/0082119 A1 | 4/2008 | Vitullo | |
| 2013/0268007 A1* | 10/2013 | Rezach | A61B 90/06 606/279 |
| 2017/0065430 A1 | 3/2017 | Singh | |
| 2017/0189121 A1* | 7/2017 | Frasier | A61B 5/067 |
| 2017/0231709 A1* | 8/2017 | Gupta | A61B 34/25 600/424 |
| 2019/0117128 A1 | 4/2019 | Chen et al. | |
| 2019/0239797 A1 | 8/2019 | Tsang et al. | |
| 2019/0388173 A1 | 12/2019 | Pak et al. | |

* cited by examiner

*Primary Examiner* — Olivia C Chang
(74) *Attorney, Agent, or Firm* — David Meibos; Maywood IP Law

(57) ABSTRACT

A surgical device for intraoperative angle measurements during surgery. The surgical device includes a shaft having a bone probe configured to remain in contact with cortical bone of the patient while a user orients the shaft to a desired orientation. The device includes a housing having an electronic circuit configured to measure an orientation angle. The electronic circuit may include: an input device configured to receive user input data; a measurement circuit configured to measure a change in orientation of the shaft in relation to a reference axis; a control circuit coupled to the input device and measurement circuit and configured to determine the orientation angle of the shaft relative to the reference axis; and an output device configured to communicate the orientation angle to the user. The device includes a power supply configured to provide power to the electronic circuit.

23 Claims, 9 Drawing Sheets

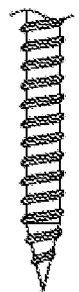 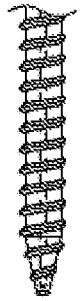 
Fig. 8A     Fig. 8B     Fig. 8C
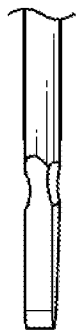 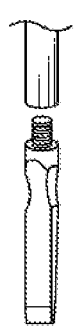
Fig. 8D     Fig. 8E

INTRAOPERATIVE ANGLE MEASUREMENT APPARATUS, SYSTEM, AND METHOD

CROSS-REFERENCE TO RELATED APPLICATIONS

The present application claims the benefit of U.S. Provisional Patent Application Ser. No. 63/117,176, entitled SPINE ANGLE AND RULER, filed on Nov. 23, 2020, which is incorporated by reference as though set forth herein in its entirety.

TECHNICAL FIELD

The present disclosure relates to surgical systems, methods, instruments, and devices. More specifically, the present disclosure relates to improved surgical systems, methods, devices, and instruments for determining and/or confirming an angle for a structure within a patient intraoperatively.

BACKGROUND

Advancements in medical imaging technology enables a doctor/surgeon to obtain precise information about the location, position, orientation, and relation of internal structures of a patient before a surgical procedure. The medical images facilitate preoperative planning for surgical procedures.

However, during a surgical procedure obtaining the same level of precision and information about internal structures of the patient is not readily available. Typically, if a surgeon wants to confirm the location and/or orientation of unexposed structures of the patient during a procedure the surgeon may rely on medical imaging technologies available in an operating room during the procedure. However, access to such medical imaging technologies in the operating room during the procedure may not be practical or feasible due to the high costs of such equipment. In addition, stopping a surgical procedure to take intraoperative images of the patient interrupts the surgical procedure, can require reconfiguration of the surgical field, and extends the duration of the procedure. Extended procedures can require a patient to remain sedated with can increase risks of complications with the success of the procedure.

Accordingly, a need exists for improved intraoperative angle measurement apparatus, system, and method that enable a surgeon to take or confirm angles for use with implant trajectories without using expensive disruptive medical imaging technologies.

SUMMARY

The various apparatus, devices, systems, and/or methods of the present disclosure have been developed in response to the present state of the art, and in particular, in response to the problems and needs in the art that have not yet been fully solved by currently available technology. One general aspect of the present disclosure can include a surgical device for intraoperative angle measurements during surgery on a patient. The surgical device may include a shaft that may include: a proximal end, and a distal end. The shaft may include a bone probe configured to engage and remain in contact with cortical bone of the patient while a user orients the shaft to a desired orientation. The device includes a housing coupled to the shaft, the housing may include: an electronic circuit configured to measure an orientation angle, the electronic circuit may include: an input device configured to receive user input data; a measurement circuit configured to measure a change in orientation of the shaft in relation to a reference axis; a control circuit coupled to the input device and measurement circuit and configured to determine the orientation angle of the shaft relative to the reference axis; an output device coupled to the control circuit and configured to communicate the orientation angle to the user. The device includes a power supply configured to provide power to the electronic circuit.

Implementations may include one or more of the following features. The surgical device may include a calibration circuit configured to determine a reference axis for the electronic circuit, the reference axis being perpendicular to a horizontal plane of a surgical field. The housing may include a planar surface and the electronic circuit determines the horizontal plane based on the planar surface resting on skin of the patient and substantially centered above a patient's spine of a patient in a prone position and based on a zero-out input signal from a user. The calibration circuit determines the reference axis in response to a zero-out input signal from a user. The electronic circuit may include a sensor configured to determine a horizontal plane and the electronic circuit determines the reference axis relative to the horizontal plane. The surgical device may include a linear measurement circuit configured to measure a linear distance between the surgical device and a second surgical device.

The output device may include an audio output device configured to provide one or more audio signals that communicate the orientation angle. The electronic circuit determines the reference axis based on the data for the reference axis. The measurement circuit may include a sensor configured to detect a change in orientation of the shaft. The measurement circuit is configured to measure an orientation of the shaft in response to user input data. The measurement circuit is configured to measure an orientation of the shaft as a user tilts the shaft to a desired orientation. The shaft may include a head near the proximal end, the head configured to receive a strike and the bone probe is configured to penetrate cortical bone in response to the strike. The shaft is cannulated from the proximal end to the distal end and configured to accept one or more of a k-wire, a bone bore, an awl, a pedicle probe, a pedicle implant, and a pedicle inserter.

One general aspect of the present disclosure can include a surgical device for intraoperative angle measurements during surgery on a patient that includes a shaft that may include: a proximal end; and a distal end opposite the proximal end, the distal end may be configured to contact cortical bone of a patient. The device includes an electronic circuit coupled to the shaft, the electronic circuit may be configured to measure an orientation angle, the electronic circuit may include: a zero-out switch configured to convey a zero-out signal; a calibration circuit configured to determine a reference axis for the electronic circuit in response to the zero-out signal; a measurement circuit configured to measure an orientation of the shaft in relation to the reference axis as a user tilts the shaft to a desired orientation, the measurement circuit may include an orientation sensor; a control circuit coupled to the switch, calibration circuit, and measurement circuit and configured to determine an orientation angle of the shaft relative to the reference axis; a display device coupled to the control circuit and configured to display the orientation angle to a user. The device includes a power supply configured to provide electric current to the electronic circuit.

Implementations may include one or more of the following features. The surgical device may include: a housing that may include the electronic circuit and the power supply; a handle closer to the proximal end of the shaft; a bone probe at the distal end of the shaft; a head at the proximal end of the shaft, the head configured to accept a driving force to form a pedicle screw pilot hole in a vertebra of the patient; an angle mode switch configured to change an operating mode of the electronic circuit from measuring distance to measuring the orientation angle of the shaft; a distance mode switch configured to change an operating mode of the electronic circuit from measuring the orientation angle of the shaft to measuring a distance between the surgical device and a second surgical device; The power supply, electronic circuit, housing, handle, head, and shaft are each configured for single use with one patient. The orientation angle displayed to a user is accurate to within three tenths of a degree.

One general aspect of the present disclosure can include a surgical device for intraoperative angle measurements during surgery on a patient. The surgical device can include a shaft that may include: a proximal end; a distal end opposite the proximal end; and a bone probe coupled to the shaft at the distal end, the bone probe configured to engage, penetrate into, and remain in stationary contact with cortical bone of the patient while a user orients the shaft to a desired orientation. The device includes a housing coupled to the shaft near the proximal end, the housing may include: an anterior surface, a posterior surface, a superior surface, an inferior surface, and a pair of opposite lateral surfaces; a user interface configured to receive input data from a user by way of a zeroing switch and to display output data to a user on a display device; a power supply configured to provide power to the electronic circuit; and an electronic circuit configured to determine an orientation angle based on a reference axis perpendicular a horizontal plane defined by one of the surfaces of the housing during a calibration mode of the electronic circuit. The device includes a handle coaxial with the shaft and positioned between the bone probe and the proximal end of the shaft; and a head coupled to the shaft near the proximal end, the head configured to receive an axial force along the shaft from a user when the shaft is oriented at the orientation angle.

Implementations may include one or more of the following features. The surgical device where the electronic circuit enters the calibration mode in response to activation of the zeroing switch. The user interface may include: a first light configured to indicate that the orientation angle is outside a range of desired orientation angles; a second first light configured to indicate that the orientation angle is within a range of desired orientation angles; and a third light configured to indicate that the orientation angle substantially at the desired orientation angle.

BRIEF DESCRIPTION OF THE DRAWINGS

Exemplary embodiments of the disclosure will become more fully apparent from the following description and appended claims, taken in conjunction with the accompanying drawings. Understanding that these drawings depict only exemplary embodiments and are, therefore, not to be considered limiting of the scope of the appended claims, the exemplary embodiments of the present disclosure will be described with additional specificity and detail through use of the accompanying drawings.

FIGS. 8A-8E illustrate perspective views of different embodiments of a bone probe that can be used with an intraoperative angle measurement apparatus in accordance with different embodiments.

Figure 1:
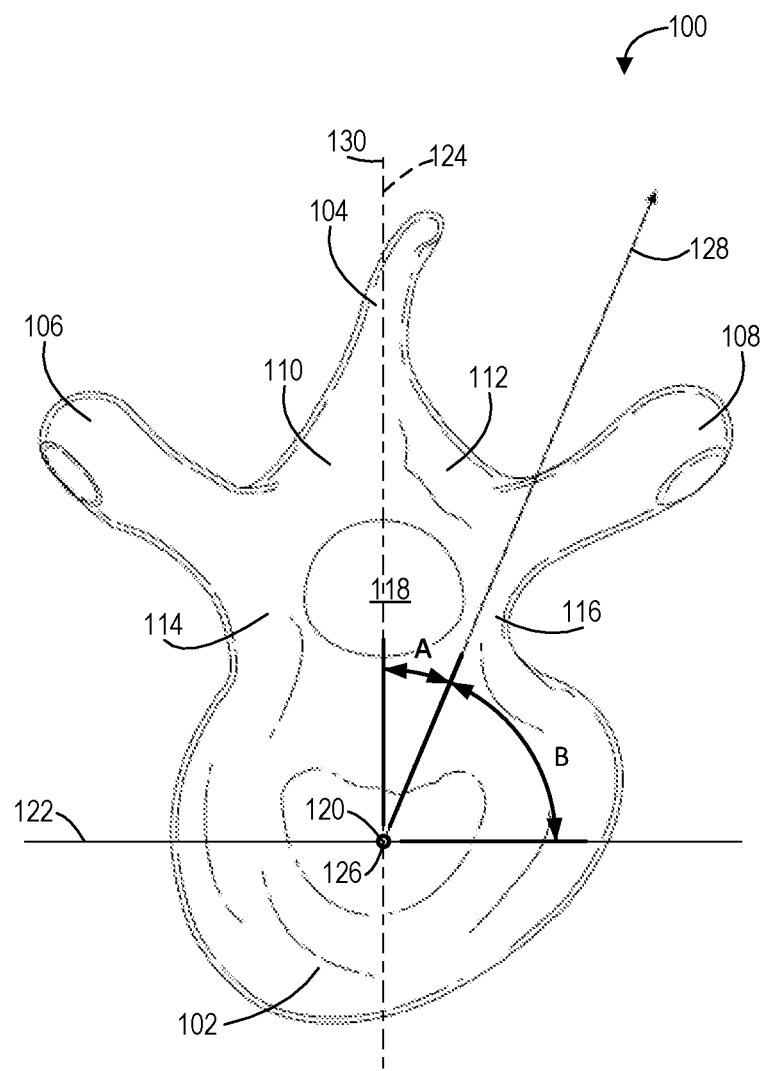
FIG. 1 is a perspective top view of vertebra bone illustrating certain parts of the vertebra bone.

It is to be understood that the drawings are for purposes of illustrating the concepts of the disclosure and may or may not be drawn to scale. Furthermore, the drawings illustrate exemplary embodiments and do not represent limitations to the scope of the present disclosure.

DETAILED DESCRIPTION

Exemplary embodiments of the present disclosure will be best understood by reference to the drawings, wherein like parts are designated by like numerals throughout. It will be readily understood that the components of the present disclosure, as generally described and illustrated in the Figures herein, could be arranged and designed in a wide variety of different configurations. Thus, the following more detailed description of the embodiments of the apparatus and method, as represented in the Figures, is not intended to limit the scope of the present disclosure, as claimed in this or any other application claiming priority to this application but is merely representative of exemplary embodiments of the present disclosure.

Standard medical planes of reference and descriptive terminology are employed in this disclosure. While these terms are commonly used to refer to the human body, certain terms are applicable to physical objects in general. A standard system of three mutually perpendicular reference planes is employed. A sagittal plane divides a body into right and left portions. A coronal plane divides a body into anterior and posterior portions. A transverse plane divides a body into superior and inferior portions. A mid-sagittal, mid-coronal, or mid-transverse plane divides a body into equal portions, which may be bilaterally symmetric. The intersection of the sagittal and coronal planes defines a superior-inferior or cephalad-caudal axis. The intersection of the sagittal and transverse planes defines an anterior-posterior axis. The intersection of the coronal and transverse planes defines a medial-lateral axis. The superior-inferior or cephalad-caudal axis, the anterior-posterior axis, and the medial-lateral axis are mutually perpendicular. Anterior means toward the front of a body.

Posterior means toward the back of a body. Superior or cephalad means toward the head. Inferior or caudal means toward the feet or tail. Medial means toward the midline of a body, particularly toward a plane of bilateral symmetry of the body. Lateral means away from the midline of a body or away from a plane of bilateral symmetry of the body. Axial means toward a central axis of a body. Abaxial means away from a central axis of a body. Ipsilateral means on the same side of the body. Contralateral means on the opposite side of the body. Proximal means toward the trunk of the body. Proximal may also mean toward a user, viewer, or operator. Distal means away from the trunk. Distal may also mean away from a user, viewer, or operator. Dorsal means toward the top of the foot. Plantar means toward the sole of the foot. Antegrade means forward moving from a proximal location/position to a distal location/position or moving in a forward direction. Retrograde means backward moving from a distal location/position to a proximal location/position or moving in a backwards direction. Sagittal refers to a midline of a patient's anatomy, which divides the body into left or right halves. The sagittal plane may be in the center of the body, splitting it into two halves. Prone means a body of a person lying face down. Supine means a body of a person lying face up.

As used herein, "medical imaging" refers to a technique and process of imaging the interior or exterior of a body for clinical analysis and medical intervention, as well as visual representation of the function of some organs or tissues (physiology). Medical imaging seeks to reveal internal structures hidden by the skin and bones, as well as to diagnose and treat disease. Medical imaging may be used to establish a database of normal anatomy and physiology to make possible identification of abnormalities. Medical imaging in its widest sense, is part of biological imaging and incorporates radiology, which uses the imaging technologies of X-ray radiography, magnetic resonance imaging, ultrasound, endoscopy, elastography, tactile imaging, thermography, medical photography, nuclear medicine functional imaging techniques as positron emission tomography (PET) and single-photon emission computed tomography (SPECT). Another form of X-ray radiography includes computerized tomography (CT) scans in which a computer controls the position of the X-ray sources and detectors. Magnetic Resonance Imaging (MRI) is another medical imaging technology.

Fluoroscopy is an imaging technique that uses X-rays to obtain real-time moving images of the interior of an object. In its primary application of medical imaging, a fluoroscope allows a physician to see the internal structure and function of a patient, so that the pumping action of the heart or the motion of swallowing, for example, can be watched. This is useful for both diagnosis and therapy and occurs in general radiology, interventional radiology, and image-guided surgery. (Search "medical imaging" on Wikipedia.com Jul. 14, 2021. CC-BY-SA 3.0 Modified. Accessed Sep. 1, 2021.) Data analyzed, generated, manipulated, interpolated, collected, stored, reviewed, and/or modified in connection with medical imaging or medical image processing can be referred to herein as medical imaging data or medical image data. Measurement and recording techniques that are not primarily designed to produce images, such as electroencephalography (EEG), magnetoencephalography (MEG), electrocardiography (ECG), and others, represent other technologies that produce data susceptible to representation as a parameter graph vs. time or maps that contain data about the measurement locations. These technologies may be considered forms of medical imaging in certain disciplines. (Search "medical imaging" on Wikipedia.com Jun. 16, 2021. CC-BY-SA 3.0 Modified. Accessed Jun. 23, 2021.)

As used herein, "preoperative" or "PRE-OP" refers to any activity, method, feature, or aspect performed before a surgical procedure. As used herein, "intraoperative" or "INTRA-OP" refers to any activity, method, feature, or aspect performed during a surgical procedure. As used herein, a "fixation" or "fixation device" refers to an apparatus, instrument, structure, device, component, member, system, assembly, step, process, or module structured, organized, configured, designed, arranged, or engineered to connect two structures either permanently or temporarily. The two structures may be one or the other or both of man-made and/or biological tissues, hard tissues such as bones, teeth or the like, soft tissues such as ligament, cartilage, tendon, or the like. In certain embodiments, fixation is used as an adjective to describe a device or component or step in securing two structures such that the structures remain connected to each other in a desired position and/or orientation. Fixation devices can also serve to maintain a desired level of tension, compression, or redistribute load and stresses experienced by the two structures and can serve to reduce relative motion of one part relative to others. Examples of fixation devices are many and include both those for external fixation as well as those for internal fixation and include, but are not limited to pins, wires, Kirschner wires (K-wires), screws, anchors, bone anchors, plates, bone plates, intramedullary nails or rods or pins, implants, interbody cages, fusion cages, and the like.

As used herein, a "deploy" or "deployment" refers to an act, action, process, system, method, means, or apparatus for inserting an implant or prosthesis into a part, body part, and/or patient. "Deploy" or "deployment" can also refer to an act, action, process, system, method, means, or apparatus for placing something into therapeutic use. A device, system, component, medication, drug, compound, or nutrient may be deployed by a human operator, a mechanical device, an automated system, a computer system or program, a robotic system, or the like.

"Cortical bone" refers to a type of bone tissue. Cortical bone is a type of bone tissue typically found between an external surface of a bone and an interior area of the bone. Cortical bone is more dense and typically stronger structurally than other types of bone tissue.

As used herein, "implant" refers to a medical device manufactured to replace a missing biological structure, support a damaged biological structure, or enhance an existing biological structure. Medical implants are man-made devices. The surface of implants that contact the body may be made of, or include a biomedical material such as titanium, stainless steel, carbon fiber, another metallic alloy, silicone, polymer, Synthetic polyvinyl alcohol (PVA) hydrogels, biocompatible polymers such as PolyEther Ether Ketone (PEEK) or a polylactide polymer (e.g. PLLA) and/or others, or apatite, or any combination of these depending on what is the most functional. In some cases implants contain electronics, e.g. artificial pacemaker and cochlear implants. Some implants are bioactive, such as subcutaneous drug delivery devices in the form of implantable pills or drug-eluting stents. Orthopedic implants may be used to alleviate issues with bones and/or joints of a patient's body. Orthopedic implants are used to treat bone fractures, osteoarthritis, scoliosis, spinal stenosis, and chronic pain. Examples of orthopedic implants include, but are not limited to, a wide variety of pins, rods, screws, anchors, and plates used to anchor fractured bones while the bones heal or fuse together. (Search "implant (medicine)" on Wikipedia.com May 26, 2021. CC-BY-SA 3.0 Modified. Accessed Jun. 30, 2021.)

As used herein, "attribute" refers to any property, trait, aspect, quality, data value, setting, or feature of an object or thing.

The phrases "connected to," "coupled to and in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

In human anatomy, the vertebral column (i.e., backbone or spine) is a column typically consisting of bones and tissue, including 33 vertebrae, situated in the dorsal area of the torso. The vertebral column serves to house and protect the spinal cord in a spinal canal.

Trauma, abnormal growth, disease, tumors, degeneration, etc. can result in physiological and anatomical disorders in the spinal column and cause deformities such as spondylolisthesis, kyphosis, and scoliosis. These deformities can result in significant pain and diminished nerve function in the diseased spine.

Spinal fusion surgery can be used successfully to address spinal column disorders and to reduce pain and restore nerve function. In spinal fixation, implants can be used for fusing or immobilizing adjacent vertebrae. Spinal fixation can improve the position of the adjacent vertebrae relative to one another and can alter the overall alignment and/or curvature of the spine. Spinal fixation or instrumentation can immobilize the spine internally in order to promote fusion between vertebrae. Fusion is a process which can take up to several months or a year.

One spinal fixation technique includes using orthopedic contouring rods which run generally parallel to the spine. This technique often involves an invasive surgical procedure to expose the spine and attach pedicle screws to the pedicles of the appropriate vertebrae. The pedicle screws may be configured to receive the orthopedic contouring rod which can be bent to achieve the desired curvature of the spinal column.

Traditionally, a surgeon inserts pedicle screws through one major central incision, where muscles and other tissues are dissected off of the spine and retracted to the side to facilitate visualization of the deep spinal bones. Under direct visualization, with or without radiological imaging, pedicle screws can be placed into the pedicles of the vertebral bodies, and then rods are typically placed to connect pedicle screws from one bone to those of other bones through the tulip head of a pedicle screw.

In recent years, surgeons may place pedicle screws percutaneously through small incisions with reliance on radiographic visualization, not direct visualization. Percutaneously placed pedicle screws can potentially save the patient the significant trauma caused by the traditional open exposure of the spine through the central incision. Unfortunately, without direct visualization, pedicle screw placement is often tedious and inaccurate. Poorly placed pedicle screws can cause pain, early construct failure, or harm to the patient.

Improper screw placement and misaligned rods decrease the effectiveness of the spinal fixation and can increase surgical difficulty and time expenditure. Extended surgical procedures and related difficulties or complications are recognized as contributing influences for extended patient recovery and sub-optimal spinal fixation results.

The present disclosure discloses an intraoperative angle measurement apparatus, system, and/or method of use. Conventional medical imaging technologies enable a surgeon to gather accurate information about body parts and structures of a patient. This information can enable a surgeon to preoperatively plan the surgery and determine a desired set of steps, equipment and/or timing for the surgery.

Spinal surgeries have advanced to address a variety of spinal conditions including scoliosis, spondylosis, kyphosis, lordosis, and the like. Certain spinal procedures include the use and placement of fixation devices and/or implants connected to, deployed into, or deployed between vertebrae of the spine. A spine includes a number of vertebrae interconnected by soft tissue of the body.

FIG. 1 is a perspective top view of vertebra 100 illustrating certain parts of the vertebra. The vertebra includes a body 102, a spinous process 104, a first transverse process 106, a second transverse process 108 (other processes omitted for clarity), a first lamina 110, a second lamina 112, a first pedicle 114, a second pedicle 116, and a vertebral foramen 118. The body 102 is anterior to the spinous process 104, the first transverse process 106, the second transverse process 108, the first lamina 110, the second lamina 112, the first pedicle 114, and the second pedicle 116 which together form the vertebral arch. The vertebral foramen 118 cooperates with vertebral foramen 118 of adjacent vertebra to form a spinal canal that houses a bundle of nerves that interconnect the brain to various parts of the patient's body.

Many spinal implants, implant systems, fixation devices, and/or assemblies include deployment of one or more fixation devices, such as bone anchors or bone screws, within a pedicle of the vertebra. Such fixation devices are referred to herein as pedicle screws. It is desirable that pedicle screws be deployed coaxial with a longitudinal axis of the pedicle. Unfortunately, pedicles within a single vertebra can have different sizes, diameters, and orientations relative to other landmarks of the vertebra. Furthermore, pedicles of different vertebra can have different sizes, diameters, and orientations relative to each other and relative to other vertebra.

Fortunately, surgeons can use medical imaging technologies to determine dimensions and orientation of pedicles for each vertebra and use that information for the planning of the placement and/or deployment of pedicle fixation devices such as pedicle screws. For example, MRI and CT scans can be used. The surgeon may preoperatively determine the trajectory needed for the approach and placement/deployment of the pedicle screw for each pedicle of each vertebra.

Often this planning includes determining a desired orientation angle for the deployment of the pedicle screw. As used herein, "orientation" refers to a direction, angle, position, condition, state, or configuration of a first object, component, part, apparatus, system, or assembly relative to another object, component, part, apparatus, system, assembly, reference point, reference axis, or reference plane. "Orientation angle" refers to an angle indicating how an orientation of one apparatus, device, component, module, structure, assembly, or system relates to another apparatus, device, component, module, structure, assembly, or system. An orientation angle may be measured in degrees or radians. Those of skill in the art will appreciate that the orientation angle used during preoperative planning and during the surgery can be measured based on an accepted coordinate system of a medical imaging system calibrated or registered to the body of the patient. Often such calibration of the medical imaging system to the cardinal planes and cardinal axis of the patient includes the use of certain landmarks on the body parts of the image.

In the illustrated embodiment, the medical imaging system can be configured such that the center point 120 of the coordinate system of the medical imaging system is in the center of the body 102 of a particular vertebra 100 of a patient. Those of skill in the art will appreciate that the center point 120 could also be on the most anterior surface of the cortical wall of the body, or any other location on the vertebra 100. In one embodiment, the coordinate system includes a medial-lateral (ML) axis 122, an anterior-posterior (AP) axis 124, and a cephalad-caudal (CC) axis 126 (going into and out of the page). The ML axis 122 can lie within the coronal plane and/or may be parallel to the coronal plane. The AP axis 124 can lie within the sagittal plane and/or may be parallel to the sagittal plane, AP plane, median plane, and/or the midline plane. The CC axis 126 can be perpendicular to the transverse plane or axial plane and/or may be parallel to the transverse plane or axial plane.

Arrow 128 may be representative of a longitudinal axis of the second pedicle 116. Arrow 128 defines an angle A between the AP axis 124 and arrow 128 and an angle B between the arrow 128 and the ML axis 122. In embodiments described herein, angle A is used to represent the desired orientation angle. However, those of skill in the art appreciate that either angle A or angle B may be used to represent a desired orientation angle and one angle can be readily converted into the other by subtracting the one angle from 90 degrees. In embodiments where angle A is used to represent the desired orientation angle, the AP axis 124 serves as a reference axis 130. In embodiments where angle B is used to represent the desired orientation angle, the ML axis 122 serves as a reference axis. "Reference axis" refers to an axis positioned and/or configured to serve as a reference in measuring or determining an attribute such as an angle and/or a distance measurement. The attribute is measured with respect to the reference axis.

Advantageously, medical imaging technologies enable a surgeon to view and obtain accurate measurements of parts of the vertebra 100, such as the pedicles. Accurate measurements of pedicles can provide information about the location, orientation, diameter and length of the pedicles. This measurement information is useful to determine the type, size, and features of pedicle implants, such as pedicles screws to be used in a procedure.

Both MRI images and CT images can be used specifically to determine a location of pedicles of each vertebra of the patient. Both MRI images and CT images provide cross-sectional images of the patient and body parts of the patient. Each of these images may be referred to as a slice or "cut" because it is a two-dimensional image of the three-dimensional structure. During preoperative planning or even intra-operatively a surgeon can review a CT cut for each pedicle 114, 116 of a vertebra 100. The CT imaging system may include a coordinate system overlay and/or a data reading of the orientation angle (e.g., angle A) of the longitudinal axis of each pedicle. The surgeon may note that orientation angle for use during the procedure. The orientation angle serves as the desired orientation angle for deployment of fixation devices (e.g., pedicle screws) in relation to the pedicle. Alternatively, or in addition, the surgeon may determine that the desired orientation angle for deployment is +/−1-3 degrees (or tenths of degrees) of the orientation angle reported by the CT cut. The desired orientation angle for deployment can serve as a trajectory for deployment of a pedicle screw from a posterior surface of the second lamina 112 between the spinous process 104 and second transverse process 108.

Now that the surgeon has the desired orientation angle for deployment of fixation devices within the pedicle, the surgeon works to locate the desired orientation angle for deployment when performing the surgery. This can be challenging as the surgeon may also desire to minimize the number and size of incisions and opening of wounds during the procedure. Generally, surgery on the spine that includes deployment of fixation devices in the pedicle is done using a posterior approach. The patient may lie in a prone on an operating table and the surgeon may make incisions in the skin and soft tissue of the back of the patient to gain access to the spine. Thus, the surgeon may have only a posterior view of the spinous process 104, first transverse process 106, and second transverse process 108 and the lamina connecting them.

Here too medical imaging solutions are available for use by surgeons to determine a deployment trajectory intraoperatively. However, such solutions can prohibitively expensive, can be of limited availability, increases exposure of a patient to radio or x-ray radiation used for the scan and can greatly increase the time needed for the procedure. The time can increase as the surgical field may need to be altered or reconfigured to accommodate the medical imaging equipment. However, the present disclosure provides an intraoperative angle measurement apparatus, system, and/or method of use that can determine and/or confirm that a surgeon's pedicle screws trajectory during surgery matches one predetermined based on medical imaging scans, without requiring use of medical imaging equipment during the procedure. The intraoperative angle measurement apparatus, system, and/or method of use of the present disclosure is simple to use, low-cost, and effective. In certain embodiments, the intraoperative angle measurement apparatus may be disposed of after a single use. A single spinal surgery can involve a number of vertebrae of a patient and each vertebra includes two pedicles. A surgeon may need to confirm an insertion trajectory and/or orientation angle for each of the pedicles.

It should be noted that with the patient in a prone position, the ML axis 122 may be parallel to, or extend within, the coronal plane of the patient. Generally, the coronal plane of a patient in the prone position is a horizontal plane also parallel to a floor of the operating room. Where angle A is the orientation angle used to determine an insertion trajectory for a pedicle screw and the AP axis 124 is the reference axis 130, the reference axis 130 may be perpendicular to the horizontal plane of the surgical field which may be parallel to the coronal plane of the patient.

As used herein, "surgical field," "operative field," or "operating field" refers to an area of a patient where surgery is or will be performed and includes one or more areas of a patient's body and all personnel and equipment that is used in the surgery. (Search "surgical field" on medical-dictionary.thefreedictionary.com Copyright 2021 Farlex Inc. Modified. Accessed Sep. 8, 2021.)

Figure 2A:
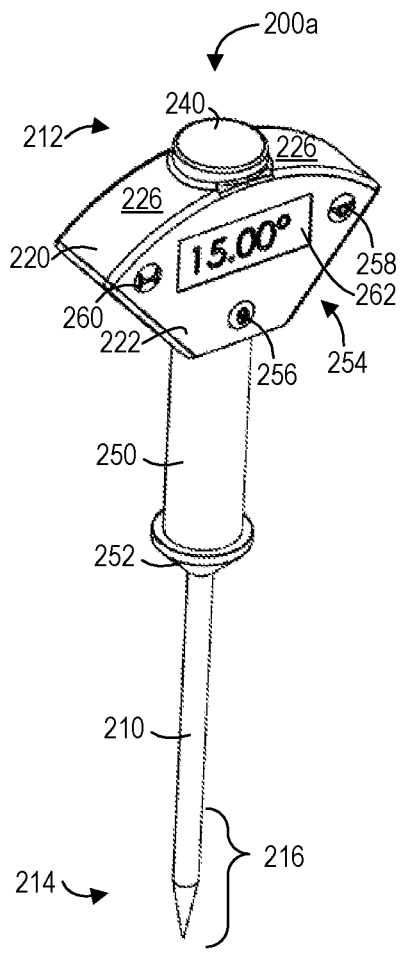
FIG. 2A is a perspective top front view of an intraoperative angle measurement apparatus according to one embodiment.
Figure 2B:
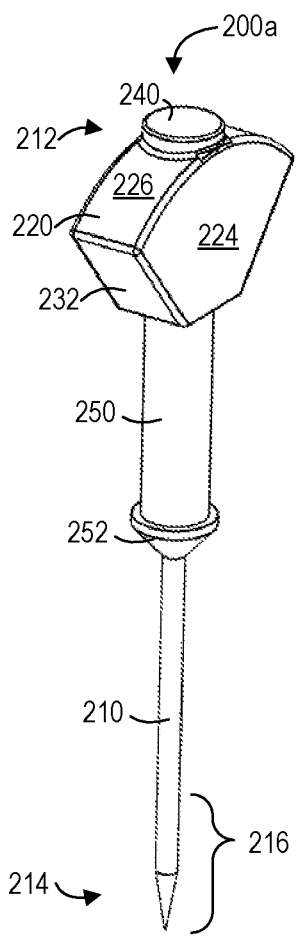
FIG. 2B is a perspective top rear view of an intraoperative angle measurement apparatus according to one embodiment.
Figure 2C:
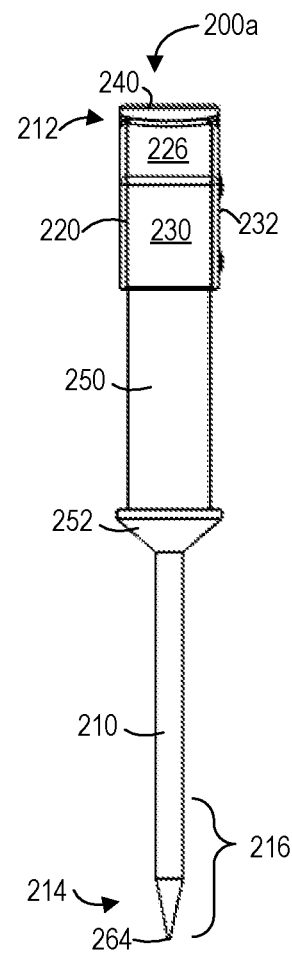
FIG. 2C is a perspective side view of an intraoperative angle measurement apparatus according to one embodiment.
Figure 2D:
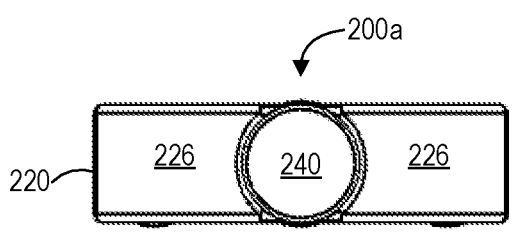
FIG. 2D is a top view of an intraoperative angle measurement apparatus according to one embodiment.
Figure 2E:
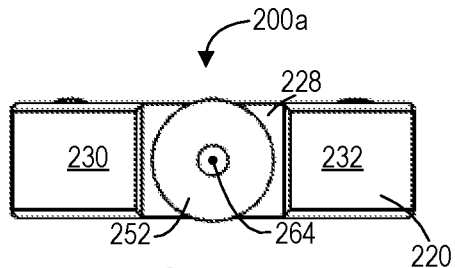
FIG. 2E is a bottom view of an intraoperative angle measurement apparatus according to one embodiment.

FIG. 2A is a perspective top front view of an intraoperative angle measurement apparatus according to one embodiment. The intraoperative angle measurement apparatus may be embodied as a surgical device 200a that include a shaft 210, a housing 220, a head 240, a handle 250, and/or an electronic circuit 300 (See FIG. 3). Those of skill in the art will appreciate that suitable intraoperative angle measurement apparatuses may have fewer components or more components than those illustrated in the embodiment of FIG. 2A.

As used herein, a "surgical device" refers to an apparatus, instrument, structure, device, component, member, system, assembly, or module structured, organized, configured, designed, arranged, or engineered to be used in connection with a surgical procedure.

As used herein, a "shaft" refers to a long narrow structure, device, component, member, system, or assembly that is structured, organized, configured, designed, arranged, or engineered to support and/or connect a structure, device, component, member, system, connected to each end of the shaft. Typically, a shaft is configured to provide rigid support and integrity in view of a variety of forces including tensile force, compression force, torsion force, shear force, and the like. In addition, a shaft can be configured to provide rigid structural support and integrity in view of a loads including axial loads, torsional loads, transverse loads, and the like. A shaft may be oriented and function in a variety of orientations including vertical, horizontal, or any orientation between these and in two or three dimensions. A shaft may be made from a variety of materials including, but not limited to, metal, plastic, ceramic, wood, fiberglass, acrylic, carbon, biocompatible materials, biodegradable materials or the like. A shaft may be formed of any biocompatible materials, including but not limited to biocompatible metals such as Titanium, Titanium alloys, stainless steel, carbon fiber, combinations of carbon fiber and a metallic alloy, stainless steel alloys, cobalt-chromium steel alloys, nickel-titanium alloys, shape memory alloys such as Nitinol, biocompatible ceramics, and biocompatible polymers such as Polyether ether ketone (PEEK) or a polylactide polymer (e.g. PLLA) and/or others, or any combination of these materials.

The shaft 210 serves to structurally interconnect parts of the surgical device 200a. In certain embodiments, the shaft 210 is elongated and has a circular cross-section. In another embodiment, the shaft 210 can have a variety of cross sectional shapes including square, rectangular, and the like. In certain embodiments, the shaft 210 includes a proximal end 212 and a distal end 214. In certain embodiments, the proximal end 212 and distal end 214 may correspond to a respective proximal end and/or distal end of the surgical device 200a. In certain embodiments, the shaft 210 has a length that enables the distal end 214 to contact cortical bone of a vertebra and the proximal end 212 extend far enough for a surgeon to comfortably operate the surgical device 200a. In certain embodiments, the shaft 210 has a length that places the proximal end 212 outside a superficial layer of skin of the patient.

The surgical device 200a can include a bone probe 216. "Bone probe" refers to a structure, device, component, assembly, or apparatus configured, designed, engineered or configured to test, explore, investigate, or probe bone, bone parts, and/or attributes of bone of a patient. In certain embodiments, a bone probe can be configured to engage and penetrate bone of the patient. In another embodiment, a bone probe can be configured to contact and remain in contact with a bone or portion of a bone while a process or step is completed. The bone probe 216 serves to contact cortical bone of a patient when the surgical device 200a is in use.

The bone probe 216 can be structured to engage and remain in contact with cortical bone of a patient when the surgical device 200a is in use. In one embodiment, the bone probe 216 can be structured to engage and remain in stationary contact with cortical bone of a patient while a user orients the shaft 210 to a desired orientation. For example, in one embodiment, the bone probe 216 may include a point on one end that contacts and may press into cortical bone of a patient. "Stationary contact" refers to a form of contact between two structures in which during the contact the structures do not translate relative to each other. In certain embodiments, a surgeon may tap on the head 240 to ensure that the bone probe 216 engages and remains in stationary contact with cortical bone as the surgical device 200a is being used.

In certain embodiments, distal end 214 of the shaft 210 includes the bone probe 216. The bone probe 216 can be integrated with the shaft 210 or coupled to the shaft 210 by way of a connector. In certain embodiments, the connector may include a threaded end and a corresponding threaded opening each of these formed in one or the other of the shaft 210 and the bone probe 216. Of course, the bone probe 216 may couple to the shaft 210 by way of a variety of other connectors and/or fasteners. In certain embodiments, the bone probe 216 is engineered and constructed to engage and remain in contact with cortical bone of a patient while a user orients the shaft 210 to a desired orientation.

The housing 220 may serve to enclose the electronic circuit 300 and a power supply. The housing 220 may be of a variety of different shapes and sizes. In certain embodiments, the housing 220 can be as small as possible to facilitate use of the surgical device 200a. The housing 220 can be coupled to the shaft 210 near or at the proximal end 212.

As used herein, a "housing" refers to a structure that serves to connect, interconnect, surround, enclose, and/or protect one or more other structural components. A housing may be made from a variety of materials including, but not limited to, metal, plastic, ceramic, wood, fiberglass, acrylic, carbon, biocompatible materials, biodegradable materials or the like. Often a housing is made from plastic due to its in expense, strength and durability. A housing may also be formed of any biocompatible materials (particularly when part of an implant), including but not limited to biocompatible metals such as Titanium, Titanium alloys, stainless steel alloys, cobalt-chromium steel alloys, nickel-titanium alloys, shape memory alloys such as Nitinol, biocompatible ceramics, and biocompatible polymers such as Polyether ether ketone (PEEK) or a polylactide polymer (e.g. PLLA) and/or others. A housing may include a frame or framework or function within a larger system, component, structure, or device.

FIGS. 2A-2E, illustrate a perspective top front view, a perspective top rear view, a perspective side view, a top view, and a bottom view of an exemplary embodiment of an intraoperative angle measurement apparatus (surgical device 200a). Referring to FIGS. 2A-2E, in the illustrated embodiment, the housing 220 has six surfaces: an anterior surface 222, a posterior surface 224, a superior surface 226, an inferior surface 228, a first lateral surface 230, and a second lateral surface 232. The surfaces may meet at edges. In the illustrated embodiment, the first lateral surface 230 and second lateral surface 232 are positioned to be a pair of opposite lateral surfaces. The first lateral surface 230 and second lateral surface 232 may extend at an obtuse angle in relation to the inferior surface 228 and engage with the superior surface 226. The angles of the first lateral surface 230 and/or second lateral surface 232 may be configured to minimize the size of the housing 220 and/or mitigate blockage of a surgeon's view into a wound the surgical device 200a is in.

The surfaces of the housing 220 can have a variety of shapes, sizes, and contours. For example, in the illustrated embodiment, the superior surface 226 may be a curved surface that includes the head 240. In certain embodiments, the head 240 is at a proximal end of the surgical device 200a and/or a proximal end 212 of the shaft 210. The head 240 may include a planar surface and have a round cross-section.

The head 240 may serve as a contact point for a surgeon to apply an axial force to the surgical device 200a. In the illustrated embodiment, the head 240 is coupled to the shaft 210 at the proximal end 212 and a center of the head 240 may align with a longitudinal axis of the surgical device 200a and/or shaft 210. A surgeon may apply the axial force to the head to cause the bone probe 216 to penetrate into the cortical bone of the patient. The axial force may be applied when the shaft 210 is oriented at a desired orientation angle. A surgeon may apply the axial force by striking or pressing the head 240 with the surgeon's hand or fingers or with an instrument such as a mallet or hammer. In one embodiment, the shaft 210 includes the head 240 near the proximal end 212. The head 240 may be configured to receive a strike and the bone probe 216 may be configured to penetrate cortical bone of a patient in response to the strike.

In certain embodiments, a surgeon may apply a driving force to the head 240 and the driving force may create a pedicle screw pilot hole in a vertebra of the patient. The surgeon may apply the driving force when the surgical device 200a is at a desired orientation angle. In this manner, the surgeon can create a pedicle screw pilot hole at the desired orientation angle. The pedicle screw pilot hole can establish a desired pedicle screw trajectory for subsequent deployment of the pedicle screw. "Pilot hole" refers to a hole, void, opening, channel, space, or passage that extends from one side of a structure into the structure. A pilot hole can serve as a guide for a fixation device subsequently placed into the pilot hole. A pilot hole can facilitate deployment of the fixation device within the structure.

In certain embodiments, the bone probe 216 is configured to penetrate into cortical bone of a patient. In particular, the bone probe 216 may include a point at its distal end and the point may enable the bone probe 216 to penetrate the cortical bone in response to an axial force from a user.

The handle 250 serves as a convenient structure for handling, manipulating, and using the surgical device 200a. In certain embodiments, the handle 250 is coaxial with the shaft 210 and positioned between the bone probe 216 and the proximal end 212 of the shaft 210. Of course, the handle 250 may be positioned at other location on the surgical device 200a and/or other parts of a surgical device 200a may serve as a handle 250. As used herein, a "handle" refers to a structure used to hold, control, or manipulate a device, apparatus, component, tool, or the like. A "handle" may be designed to be grasped and/or held using one or two hands of a user. In the illustrated embodiment, the handle 250 may include a flange 252 at a distal end of the handle 250. The flange 252 may press against soft tissue of a patient and keep the soft tissue from contacting or surrounding the handle 250. In certain embodiments, the flange 252 may be conical in shape.

In certain embodiments, the surgical device 200a can be used with cortical bone that is not fully exposed. In certain embodiments, the bone probe 216 and/or shaft 210 can be configured to pierce soft tissue such as muscle, skin, or ligaments until the bone probe 216 contacts a bone surface. In this manner, smaller incisions can be used with less trauma to the soft tissue. The lower trauma can lead to faster recovery times. In certain embodiments, the flange 252 can facilitate insertion of the bone probe 216 and/or shaft 210 into soft tissue for measuring an orientation angle.

Each of the surfaces may include one or more features. For example, the anterior surface 222 may include a user interface 254. The user interface 254 enables a user to input data and/or provide instructions to the surgical device 200a and receive feedback, data, output data, or output from the surgical device 200a. The user interface 254 may include a combination of one or more switches, buttons, displays, speakers, or other input devices and/or output devices.

As used herein, an "interface," "user interface," or "engagement interface" refers to an area, a boundary, or a place at which two separate and/or independent structures, members, apparatus, assemblies, components, and/or systems join, connect, are coupled, or meet and act on, or communicate, mechanically or electronically, with each other. In certain embodiments, "interface" may refer to a surface forming a common boundary of two bodies, spaces, structures, members, apparatus, assemblies, components, or phases. (search "interface" on Merriam-Webster.com. Merriam-Webster, 2021. Web. 15 Nov. 2021. Modified.) In certain embodiments, the term interface may be used with an adjective that identifies a type or function for the interface. For example, an engagement interface may refer to one or more structures that interact or connect to mechanically join or connect two separate structures, each connected to a side of the interface. In another example, a user interface may refer to one or more mechanical, electrical, or electromechanical structures that interact with or enable a user to provide user input, instructions, input signals, data, or data values and receive output, output data, or feedback.

"Data" refers to a set of information organized in a way that facilitates communication of the information to a receiver. The receiver may be a person or animal or an electronic component, circuit, assembly, or the like. Data can be represented as signal or values represented in any numbering and/or alphabet system. Data can be stored in one representation in an analog or digital format and conveyed to a receiver in another format suitable for the receiver to interpret and understand the data. Data can be organized in a structured or unstructured format. "Structured data" refers to data within a data structure that is organized according to a predefined format, protocol, or configuration such that the structure may be used to facilitate working with the data. Examples of structured data include, but are not limited to, files, databases, database records, database tables, database schemas, serialized objects, directories, and the like. "Unstructured data" refers to data stored without a particular organization, predefined format, protocol, or configuration. Examples of unstructured data include, but are not limited to, content of a text message, content of an email message, text content of a file, content of a document, and the like. Often data will be used in connection with one or more adjectives that identify a type or purpose for the data, examples include "user data", "input data", "output data", "sensor data", "patient data", "system data", and the like.

"Sensor data" refers to any data or information registered by one or more sensors. Examples of sensor data include an amount of current passing through the sensor, an amount of voltage across the sensor, an amount of electrical resistance through the sensor, an amount of strain experienced by the sensor, an acceleration vector, a deceleration vector, an orientation, an orientation angle, a direction, and the like.

"Output data" refers to data provided from one device, component, circuit, or apparatus to another device, component, circuit, or apparatus. Examples of output data can include activation of a light, activation of a switch, data values, audio signals, video signals, images, videos, and the like. "Input data" refers to data identified, used, collected, gathered, and/or generated to serve as input to another component, circuit, driver, device, manager, control circuit, storage media, storage device, or controller. The input data can be in analog or digital format and can represent a data signal and/or one or more data values.

"Input device" refers to any apparatus, device, component, module, circuit, sub-circuit, structure, electronic component, hardware, or logic configured, programmed, designed, arranged, or engineered to receive input data, input instructions, input information, input signals, or the like from an environment. Often, a user may interact with an input device to provide input information. Examples of input devices includes, but are not limited to a button, a switch, a sensor, a keyboard, a keypad, a touch screen incorporated into a graphical user interface, audio input devices such as voice recognition systems, microphones, transceivers, receivers, other types of input devices, and the like. In various embodiments, input devices can be incorporated into a user interface. "Output device" refers to any apparatus, device, component, module, circuit, sub-circuit, structure, electronic component, hardware, or logic configured, programmed, designed, arranged, or engineered to output data, instructions, information, signals, audio information, visual information, video information, or the like. Examples of output devices includes, but are not limited to one or more of a switch, a sensor, an LED, a light, a speaker, a transceiver, a transmitter, a display and the like. In various embodiments, output devices can be incorporated into a user interface.

The user interface 254 can include a zero-out switch 256 (also referred to as a Zeroing switch), an angle mode switch 258, a distance mode switch 260, and/or a display 262. "Zero-out" or "Zeroing" refers to a feature or function of a measuring device, apparatus, or circuit that adjusts or calibrates a measurement system of the measuring device to start using a new reference indicator as a zero point or state for subsequent measurements. The feature can be initiated by an electronic signal, also referred to as a zero-out signal or zero-out input signal, user input or user input data, generated in response to activation of a zero-out button or zero-out switch. A zero-out feature can be used to compensation for errors inherent in a measuring device. A zero-out feature can also be used to set a new zero state or zero point for subsequent measurements taken compensation for errors inherent in a measuring device. A variety of attributes measurable by a measuring device can be measuring using the zero-out feature including, but not limited to, weight (aka tare feature), angle, tilt, tilt axis, rotation, static acceleration, dynamic acceleration, and the like. In certain embodiments, the zero-out switch 256 may serve two functions, first to provide a zero-out input signal and second the zero-out switch 256 may serve as a power-on and/or power-off switch/button.

"Mode" refers to a state of operation for a circuit, sub-circuit, circuitry, electronic component, hardware, software, firmware, module, logic, device, button, lever, or apparatus. When a mode is activated, the circuit, sub-circuit, circuitry, electronic component, hardware, software, firmware, module, logic, device, or apparatus may perform one or more set of functions that are different from when the mode is not activated. Often "mode" is used with a modifier describing and differentiating one mode or operating state from another, for example an "operating mode" relates to a mode of operation, a "calibration mode" relates to a mode of calibrating, a "distance mode" relates to distance operations, and an "angle mode" relates to angles. "Switch" refers to a circuit, sub-circuit, circuitry, electronic component, hardware, software, firmware, module, logic, device, button, lever, or apparatus configured, programmed, designed, arranged, or engineered to close an electronic circuit and/or couple one electronic component or circuit with another. In one embodiment, the switch is configured to send a signal to another electronic component when the switch is activated ("closed").

"Display device" refers to any apparatus, device, component, module, circuit, sub-circuit, structure, electronic component, hardware, or logic configured, programmed, designed, arranged, or engineered to display, show, or present one or more visual images and/or videos to a user. A display device can use analog or digital technologies. Examples of a display device include one or more LEDs, a seven segment display, an LCD display, an LED display, and the like.

The user interface 254 can receive input data from a user by way of zeroing switch, such as zero-out switch 256 and display output data to a user on a display device (e.g., display 262). The zero-out switch 256 may convey a zero-out signal to the electronic circuit 300. The angle mode switch 258 may change an operating mode of the electronic circuit 300 from measuring distance to measuring an orientation angle of the shaft 210/surgical device 200a. The distance mode switch 260 may change an operating mode of the electronic circuit 300 from measuring an orientation angle of the shaft 210/surgical device 200a to measuring a distance between the surgical device 200a and a second surgical device. Details of the zero-out switch 256, angle mode switch 258, and/or distance mode switch 260 are discussed below.

Those of skill in the art appreciate that a variety of different user interfaces 254 can be used with the surgical device 200a. For example, a single button or switch may toggle a state, feature, or function of the surgical device 200a between an angle mode and a distance mode. Alternatively, or in addition, the user interface 254 may be a touch screen with representation of buttons or switches displayed that respond when a user touches that part of the screen.

In one embodiment, one of the surfaces (e.g., posterior surface 224) may include a door or hatch that provides access to an internal battery or other power supply for the surgical device 200a. In another example, a surface may include a port for connecting an external power supply to the surgical device 200a either for primary power or for charging an internal power supply.

FIGS. 2A-2C, and 2E illustrate a bone probe 216 with a configuration for engaging and remaining stationary on a bone surface of a patient. In one embodiment, the bone probe 216 may include a point/tip 264. The point/tip 264 may be at the distal end 214 of the shaft 210 and/or surgical device 200a.

Figure 2F:
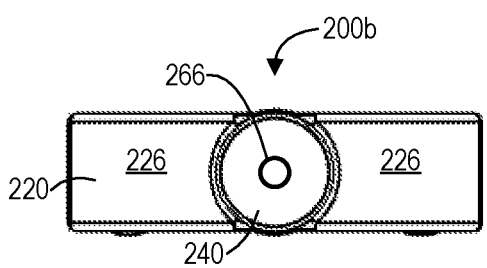
FIG. 2F is a top view of an intraoperative angle measurement apparatus according to one embodiment.
Figure 2G:
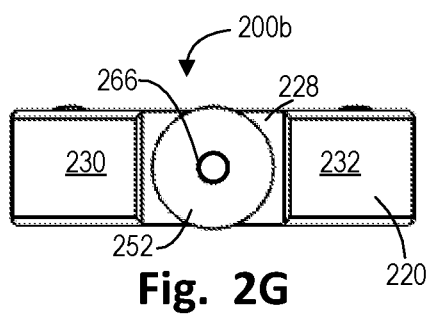
FIG. 2G is a bottom view of an intraoperative angle measurement apparatus according to one embodiment.

FIGS. 2F, 2G illustrate a top view and a bottom view of an alternative embodiment for an intraoperative angle measurement apparatus, surgical device 200b. The surgical device 200b may have many structures, features, and functions, operations, and configuration similar or identical to those of the surgical device 200a described in relation to FIGS. 2A-2E, like parts are identified with the same reference numerals. Accordingly, the surgical device 200b may include a shaft 210, a housing 220, a head 240, a handle 250, and/or an electronic circuit 300 (See FIG. 3).

In the illustrated embodiment, the surgical device 200b differs from the surgical device 200a because the surgical device 200b includes an opening 266 that extends from a proximal end of the surgical device 200b to a distal end of the surgical device 200b. Alternatively, or in addition, the opening 266 may extend from a proximal end 212 to a distal end 214 of the shaft 210. In this manner, the shaft 210 may be cannulated. The opening 266 may be coaxial with, and may pass through, the head 240, housing 220, shaft 210, handle 250, flange 252, and/or bone probe 216. In the illustrated embodiment, the surgical device 200b may serve as a cannula that can be used for one or more steps of a surgical procedure (e.g., pedicle screw deployment). The opening 266 may have a diameter that accepts passage of a variety of instruments that a surgeon may use as part of a procedure to deploy a fixation device (e.g., a pedicle screw).

As used herein, an "opening" refers to a gap, a hole, an aperture, a port, a portal, a space or recess in a structure, a void in a structure, or the like. In certain embodiments, an opening can refer to a structure configured specifically for receiving something and/or for allowing access. In certain embodiments, an opening can pass through a structure. In other embodiments, an opening can exist within a structure but not pass through the structure. An opening can be two-dimensional or three-dimensional and can have a variety of geometric shapes and/or cross-sectional shapes, including, but not limited to a rectangle, a square, or other polygon, as well as a circle, an ellipse, an ovoid, or other circular or semi-circular shape. As used herein, the term "opening" can include one or more modifiers that define specific types of "openings" based on the purpose, function, operation, position, or location of the "opening." As one example, a "fastener opening" refers to an "opening" adapted, configured, designed, or engineered to accept or accommodate a "fastener."

In one embodiment, the opening 266 may be sized to accept one or more of a K-wire, a bone bore, an awl, a pedicle probe, a pedicle implant, and/or a pedicle inserter. A surgeon may pass one or more of these example instruments through the opening 266 as part of a pedicle screw placement procedure or step. The surgeon may use the surgical device 200b to determine, or confirm, a desired orientation (e.g., desired orientation angle) for the location of the pedicle and use one or more of these example instruments to mark, identify, or implement an insertion trajectory for one or more pedicle screws into the pedicle of the vertebra 100.

"Bone bore" refers to an apparatus, instrument, structure, device, component, member, system, assembly, or module structured, organized, configured, designed, arranged, or engineered to form a bore, hole, or tunnel into and/or through bone of a patient. Examples of a bone bore include a surgical drill bit, an awl, a pedicle probe, and the like. "Pedicle probe" refers to an apparatus, instrument, structure, device, component, member, system, assembly, or module structured, organized, configured, designed, arranged, or engineered to probe and/or explore a pedicle structure of a patient's bone. In certain embodiments, a pedicle probe can be used to determine where the pedicle is and how its configuration relates to other structures in the body. In certain embodiments, a pedicle probe can be inserted into a pedicle and pressed through bone of the pedicle to form a pilot hole through the pedicle for a fixation device.

In one embodiment, a shaft 210 may extend through the head 240 and include an interface that enables the shaft 210 to couple to one or more other instruments that can be used for deployment of a pedicle screw. For example, a surgeon may connect the shaft 210 to a surgical drill and the bone probe 216 may include a drill bit configuration at the distal end such that the surgical device 200b may be rotated about its longitudinal axis to create a hole in bone of a patient, and specifically in certain embodiments, to create a hole in a pedicle of a patient.

The embodiments of FIGS. 2A-2E and 2F-2G are but two examples of a plurality of examples of embodiments that can be implemented within the scope of the claims that accompany this disclosure. In another embodiment, an intraoperative angle measurement apparatus, surgical device, can be made according to the claims of the present disclosure such that the surgical device serves one or two features or functions during a single surgical procedure, but then can be discarded once it is no longer needed. Such an embodiment, may be referred to as a single use surgical device or single use device because it is designed, engineered, and/or fabricated for a single surgical procedure; for a single use with one patient. It should be noted that in certain embodiments, a single use device, single use surgical device may be used to facilitate insertion of a plurality of fixation devices (e.g., pedicle screws) for one patient.

"Single use" or "single use device" refers to a structure, assembly, system circuit, sub-circuit, circuitry, electronic component, hardware, software, firmware, module, logic, device, button, lever, or apparatus configured, programmed, designed, arranged, or engineered to be used one time to performed one or more functions, features, or operations. In certain embodiments, a single use device may include components, structures, or parts that are specifically engineered for use only one time. In certain embodiments, a single use device may include less expensive components that satisfy requisite specifications for use one time but are not expected to meet those same specifications after the single use. For example, a single use device may include a battery power supply with sufficient charge for one use but not more than one use. This configuration may enable the single use device to include a smaller component, like a battery, less reinforcement or use less expensive and/or less durable materials for components of the single use device. In certain embodiments, a single use device can be disposed of after the single use.

In one embodiment of a single use surgical device, the power supply, electronic circuit 300, housing 220, head 240, shaft 210 and/or other components may be specifically engineered to provide the features, functions, and aspects of a surgical device 200a,b but only for a single surgical procedure. For example, the power supply may be large enough to function during the single surgical procedure, but not large enough for a second surgical procedure. Similarly, the materials used, and the manner of fabrication may be such that the other structural components may function for a single surgical procedure, but not a subsequent surgical procedure. This may mean that the fabrication costs are reduced and the cost of the surgical device 200a,b is also reduced.

While the surgical device 200a,b may be a single use surgical device, certain functionality may provide an acceptable level of accuracy. For example, in such an embodiment, the orientation angle displayed to a user may be accurate to within three tenths of a degree. Such a level of accuracy may be sufficient for confirming an insertion trajectory for a pedicle screw while at the same time worth disposing of after the surgical procedure. While a single use surgical device may result in medical waste following the surgical procedure, the savings in costs of materials, fabrication, and distribution of the single use surgical device and advantage the single use surgical device provides for intraoperative angle/distance measurement over conventional high expense medical imaging technologies may support the trade-off.

Figure 3:
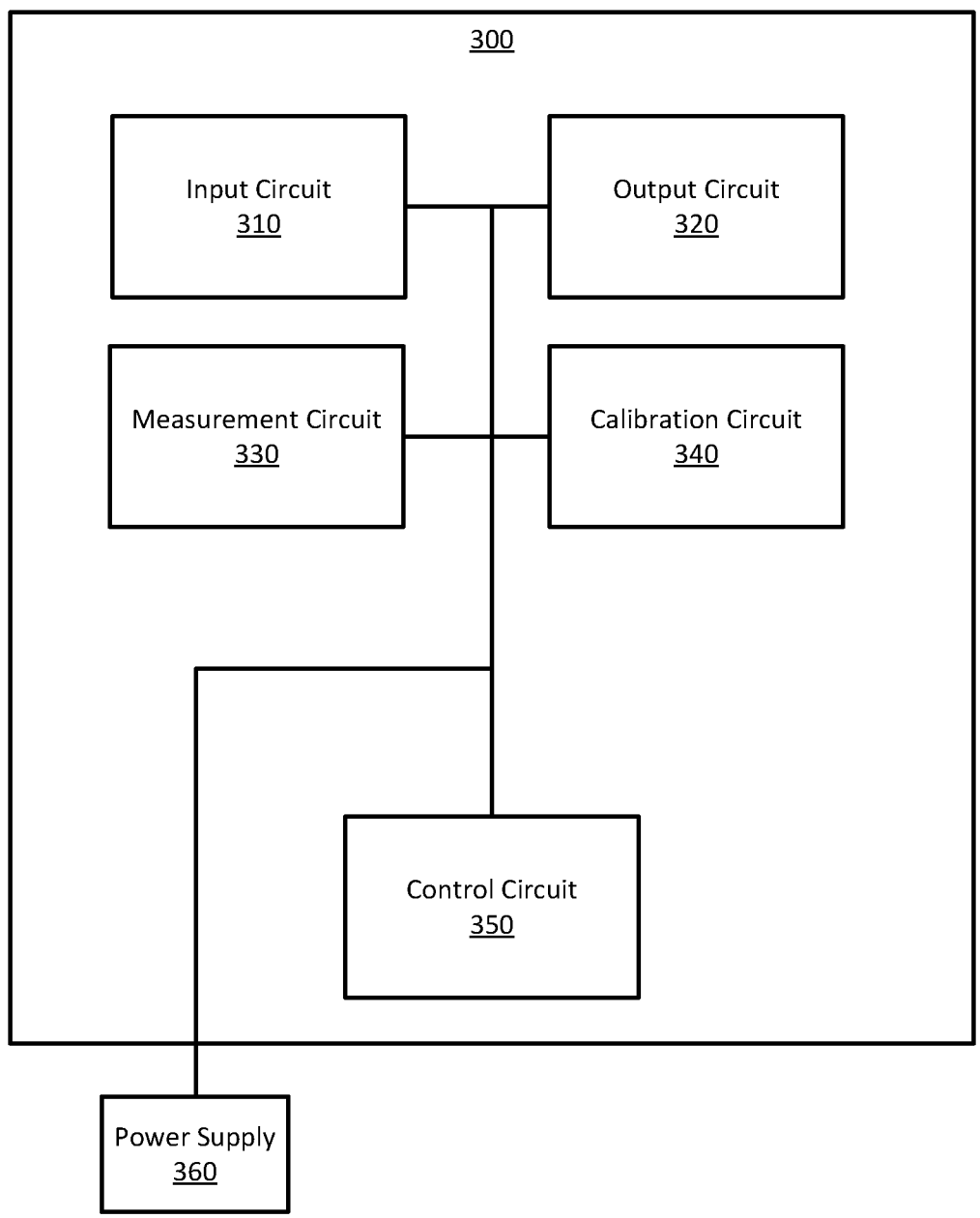
FIG. 3 is a block diagram of an exemplary electronic circuit according to one embodiment.

FIG. 3 is a block diagram of an exemplary electronic circuit 300 according to one embodiment. The electronic circuit 300 can be used with embodiments described herein. For example, in one embodiment, the housing 220 may include the electronic circuit 300. The electronic circuit 300 serves to measure an orientation angle. Specifically, the electronic circuit 300 may measure an orientation angle of the shaft 210 and/or the surgical device 200a,b. In certain embodiments, an electronic circuit 300 may also measure a distance, as described in more detail below. In one embodiment, the electronic circuit 300 may serve as a controller for the surgical device 200a,b.

"Controller" refers to any hardware, device, component, element, or circuit configured to manage, implement, or control the features, functions, and/or logic for a device, component, apparatus, or system, and may comprise one or more processors, programmable processors (e.g., FPGAs), ASICs, micro-controllers, electronic circuits, or the like. "Logic" refers to machine memory circuits, non-transitory machine readable media, and/or circuitry which by way of its material and/or material-energy configuration comprises control and/or procedural signals, and/or settings and values (such as resistance, impedance, capacitance, inductance, current/voltage ratings, etc.), that may be applied to influence the operation of a device. Magnetic media, electronic circuits, electrical and optical memory (both volatile and nonvolatile), and firmware are examples of logic. Logic specifically excludes pure signals or software per se (however does not exclude machine memories comprising software and thereby forming configurations of matter). "Electronic Circuit" or "Circuitry" refers to any circuit, sub-circuit, electronic component, hardware, module, logic, device, or apparatus configured, programmed, designed, arranged, or engineered to perform one or more features, functions, steps, methods, processes of portions thereof. In certain embodiments, an electronic circuit or circuitry may include electrical circuitry having at least one discrete electrical circuit, electrical circuitry having at least one integrated circuit, electrical circuitry having at least one application specific integrated circuit, circuitry forming a state machine, circuitry forming a general purpose computing device configured by a computer program (e.g., a general purpose computer configured by a computer program which at least partially carries out processes or devices described herein, or a microprocessor configured by a computer program which at least partially carries out processes or devices described herein), circuitry forming a memory device (e.g., forms of random access memory), circuitry forming a communications device (e.g., a modem, communications switch, or optical-electrical equipment), or the like. An electronic circuit or circuitry may include one or more modifiers that identify one or more particular functions, features, aspects, attributes, advantages, roles, purposes, modes of operation, or operations and/or particular structures relating to the electronic circuit, circuit, or circuitry. Examples of such modifiers applied to a circuit or circuitry, include, but are not limited to, "control circuit," "test circuit," "calibration circuit," "sensing circuit," "output circuit," "input circuit," "I/O circuit," "measurement circuit," "display circuit," and the like.

In one embodiment, the electronic circuit 300 may include one or more of an input circuit 310, an output circuit 320, a measurement circuit 330, a calibration circuit 340, and a control circuit 350. The electronic circuit 300 may be coupled with a power supply 360.

The input circuit 310 receives input data, instructions, signals or commands from someone or something outside the electronic circuit 300. In one embodiment, an input circuit 310 can be a single input device. Alternatively, or in addition, the input circuit 310 can be a plurality of interconnected or intercommunicating devices, such as input devices. In one embodiment, the input circuit 310 is an input device that receives user input data.

The output circuit 320 sends, conveys, signals, and/or communicates output data, instructions, signals or commands to someone or something outside the electronic circuit 300 (e.g., a user or operator). In one embodiment, an output circuit 320 can be a single output device. Alternatively, or in addition, the output circuit 320 can be a plurality of interconnected or intercommunicating devices, such as output devices. In one embodiment, the output circuit 320 is an output device that communicates output data (e.g., an orientation angle) to a user or another device. In certain embodiments, the output circuit 320 and/or output device is coupled to the control circuit 350. The output circuit 320 and/or output device may be configured to communicate the orientation angle determined by the electronic circuit 300 to a user.

The measurement circuit 330 is a circuit or device or module that measures a change in orientation of the shaft 210 (or surgical device 200) in relation to a reference axis. In one embodiment, the reference axis is an axis such as the reference axis 130 described in relation to FIG. 1. In another embodiment, the reference axis may be an axis determined by another circuit, sensor, or component of the surgical device 200. Alternatively, or in addition, the reference axis may be and stored in a storage media of the surgical device 200 for subsequent use. For example, the reference axis may be predetermined during fabrication, during operating room preparations, or another time before the surgical device 200 is used for a procedure. The data and/or value used to define and represent the reference axis may be stored in a storage media that can be included in the surgical device 200.

In one embodiment, the measurement circuit 330 can measure an orientation of the shaft 210 in relation to a reference axis 130 as a user tilts the shaft 210 to a desired orientation. The measurement circuit 330 may include an orientation sensor, described in more detail below.

As used herein, a "sensor" refers to a device, component, circuit, system, chip, hardware, logic, or circuitry configured to detect, sense, and/or measure an attribute, feature, or characteristic of an environment, a space, a thing, an apparatus, a circuit, a component, and/or the like. Examples of a sensor include but are not limited to an accelerometer, a goniometer, a digital goniometer, a tiltmeter, an inclinometer, a potentiometer, a geomagnetic sensor, an acoustic sensor, a dynamic acceleration sensor, a dynamic acceleration sensor, a gyroscope, a temperature sensor, and the like. In certain embodiments, a single sensor may detect, sense, and/or measure a single attribute, feature, or characteristic. In other embodiments, a single sensor may detect, sense, and/or measure a plurality of attributes, features, and/or characteristics. A sensor can be made up of analog, digital, electrical, mechanical, and/or electromechanical components and may function with or without an external power source. A sensor can employ a variety of technologies in order to detect, sense, and/or measure an attribute, feature, or characteristic. For example, certain sensors may use electronic signals, radio signals, electromagnetic signals, magnetic signals, light signals, sound signals, and the like. Certain sensors may include a receiver and/or a transmitter of signals or waves for performing the sensing feature. Often a sensor is configured to communicate information about a detected, sensed, and/or measured an attribute, feature, or characteristic to another electronic component or device. The information may be communicated using a wired connection or a wireless connection.

The calibration circuit 340 is a circuit or device or module that determines a reference axis, such as reference axis 130. In certain embodiments, the calibration circuit 340 may compute, calculate, or determine the reference axis 130. Alternatively, or in addition, the calibration circuit 340 may retrieve the reference axis 130 and/or a representation of the reference axis 130 from a storage media. In certain embodiments, the calibration circuit 340 may determine a reference axis in response to an input signal, such as a zero-out signal. In other embodiments, the calibration circuit 340 determine a reference axis based on signals or input from one or more sensors.

The control circuit 350 is coupled to the input circuit 310, the output circuit 320, the measurement circuit 330, and the calibration circuit 340. The control circuit 350 may manage the other circuits in the electronic circuit 300. Alternatively, or in addition, the control circuit 350 may determine an orientation angle (e.g., angle A and/or angle B) of the shaft 210/surgical device 200 relative to the reference axis 130. "Control circuit" refers to a circuit, sub-circuit, circuitry, electronic component, hardware, software, firmware, module, logic, device, or apparatus configured, programmed, designed, arranged, or engineered to direct, manage, oversee, and/or control the operation of one or more other circuits or components.

The power supply 360 couples to the electronic circuit 300 and provides power to operate the electronic circuit 300. In one embodiment, the power supply 360 is a battery. The battery may be replaceable or nonreplaceable. In another embodiment, the power supply 360 may be a supercapacitor with sufficient power to supply the electronic circuit 300 with power for use in a single surgical procedure. "Power supply" refers to an electronic system, component, assembly, apparatus, or device configured to provide electrical power in the form of current to one or more devices, components, assemblies, and/or electronic circuits. Examples of a power supply include a battery, a wall power outlet socket, a power generator, and the like.

Figure 4:
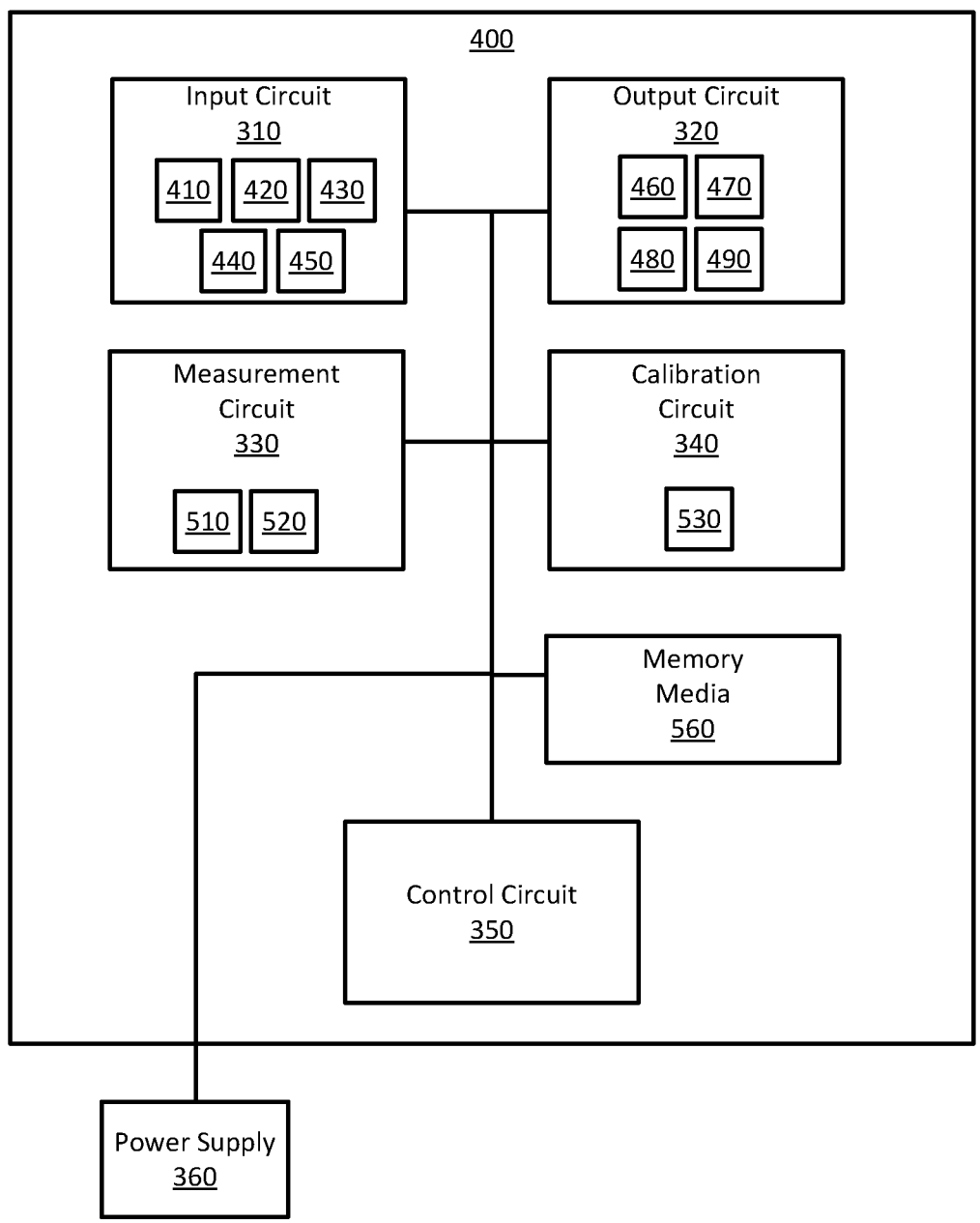
FIG. 4 is a block diagram of an exemplary electronic circuit according to certain embodiments.

FIG. 4 is a block diagram of an exemplary electronic circuit according to certain embodiments. Those of skill in the art will appreciate that an intraoperative angle measurement apparatus according to the present disclosure can include one or two features and/or functions of a plurality of features and functions. The number of features and/or functions provided by embodiments of an intraoperative angle measurement apparatus can change the configuration of the electronic circuit within the intraoperative angle measurement apparatus. The exemplary electronic circuit 400 illustrates certain features, devices, components, sub-circuits, or modules that can be implemented in certain embodiments.

FIG. 4 illustrates an alternative embodiment for an exemplary electronic circuit 400 that can be used. The electronic circuit 400 may have many structures, features, and functions, operations, and configuration similar or identical to those of the electronic circuit 300 described in relation to FIG. 3, like parts are identified with the same reference numerals. The electronic circuit 400 may include one or more of an input circuit 310, an output circuit 320, a measurement circuit 330, a calibration circuit 340, and a control circuit 350. However, certain of these components may have more or fewer features, devices, components, sub-circuits, or modules than those of the electronic circuit 300.

Those of skill in the art appreciate that the input circuit 310 and/or output circuit 320 can have different configurations in different embodiments. Examples of input devices that the input circuit 310 may include are one or more buttons 410, one or more switches 420, one or more arrow buttons 430, a keypad 440, a keyboard 450, and the like. Examples of output devices that the output circuit 320 may include are one or more displays 460, one or more speakers 470, one or more lights 480, one or more haptic feedback devices 490, and the like.

The one or more buttons 410 may be each perform (or cause to be performed) a single function or operation or one or more of the buttons 410 may perform a plurality of functions or operations. For example, one button 410 may be a power on button, another button 410 may be a power off button, or the same button 410 may serve as both a power on button and a power off button. As a further example, a single button may serve as a power on button, a power off button, and/or a reset button. The reset function may delete a previously (permanently or temporarily) stored orientation angle. Like the one or more buttons 410 the one or more switches 420 may each perform (or cause to be performed) a single function or a plurality of functions.

In certain embodiments, pressing a certain input button 410 may lock or freeze (temporarily) the current orientation angle value displayed on a display for review or use during a procedure. In one embodiment, a button 410 or switch 420 may be activated by a user shaking the surgical device 200, the shaking action may serve as user input data instructing the electronic circuit 400 to power on the electronic circuit 400. In one embodiment, one of the one or more switches 420 may be a zero-out switch configured to convey a zero-out signal. The zero-out signal may be communicated to a calibration circuit 340. The calibration circuit 340 may initiate a calibration feature in response to the zero-out signal. The calibration feature may include determining a reference axis for the electronic circuit 400.

The one or more arrow buttons 430 can be used to input a desired/target orientation. The electronic circuit 400 may store the desired/target orientation for comparison to measured orientation angles as a user operates the surgical device 200. For example, the input circuit 310 may include an up arrow indicating an increase in the degrees or tenths or hundredths of a degree that a user wants to set as the desired/target orientation. Similarly, the input circuit 310 may include a down arrow indicating a decrease in the degrees or tenths or hundredths of a degree that a user wants to set as the desired/target orientation. Of course either the up arrow or the down arrow may skip tens of degrees or tenths or hundredths based on how long a user presses and holds the respective arrow.

A keypad 440 may also be included and can be used for input data. For example, the keypad 440 could be a numeric keypad and a user may enter a number representing a desired/target orientation. Alternatively, or in addition, the input circuit 310 may include a keyboard 450 and the user may use the keyboard 450 to enter a number representing a desired/target orientation. In certain embodiments, an electronic circuit 400 can be configured to store a desired/target orientation for a plurality of vertebrae and a label for the associated vertebrae.

The output circuit 320 may include one or more displays 460. One display 460 may show the current orientation angle of the surgical device 200. Another display 460 may show a desired/target orientation. Another display 460 may accept touch input and may therefore display graphical input devices, such as switches, buttons, arrows, and the like. The output circuit 320 may have one or more displays 460 and/or a single display 460 may show different information on different parts of the display 460. In certain embodiments, the display 460 include numbers, letters, or symbols and a level of contrast that facilitates quick and clear reading by a surgeon during a procedure.

The one or more speakers 470 can be used by the electronic circuit 400 to provide audible output data. The one or more speakers 470 may be used for a variety of audio feedback and/or output. For example, in one embodiment, the one or more speakers 470 may provide a distinctive beep or sound when an electronic circuit 400 has been zeroed out. Alternatively, or in addition, the one or more speakers 470 can be used to provide an audible sound or set of sounds or audio signals with distinctive changes in tone and/or frequency to indicate when a current orientation angle of the surgical device 200 gets closer to, further away from, and/or reaches a desired/target orientation.

The one or more lights 480 can be used by the electronic circuit 400 to provide visual output data. The one or more lights 480 may be used for a variety of visual feedback and/or output. For example, in one embodiment, the one or more lights 480 may illuminate, flash, or blink with or without a distinctive pattern to indicate when an electronic circuit 400 has been zeroed out. Alternatively, or in addition, the one or more lights 480 can be used to illuminate, flash, or blink with or without a distinctive pattern to indicate when a current orientation angle of the surgical device 200 gets closer to, further away from, and/or reaches a desired/ target orientation.

The one or more haptic feedback devices 490 can be used by the electronic circuit 400 to provide haptic output data and/or haptic feedback. The one or more haptic feedback devices 490 may be used for a variety of haptic feedback and/or output. For example, in one embodiment, the one or more haptic feedback devices 490 may activate at a single or a plurality of levels or rates and/or patterns to indicate when an electronic circuit 400 has been zeroed out. Alternatively, or in addition, the one or more haptic feedback devices 490 can activate with or without a distinctive pattern to indicate when a current orientation angle of the surgical device 200 gets closer to, further away from, and/or reaches a desired/ target orientation.

Those of skill in the art will appreciate that the output circuit 320 can communicate the orientation angle to a user using a variety of methods, including a visual display of an angle value in degrees, a distinct audible signal(s) when the surgical device 200 is at an orientation angle, visual indicators, and/or a haptic feedback signal and/or pattern.

As with the input circuit 310 and output circuit 320, those of skill in the art appreciate that the measurement circuit 330 and/or calibration circuit 340 can have different configurations in different embodiments. The measurement circuit 330 measures a change in orientation angle of a shaft 210 in relation to a reference axis. In certain embodiments, the measurement circuit 330 measures the orientation angle of the shaft 210 relative to the reference axis in response to input data from a user (e.g., pressing or activating a button or switch). Alternatively, or in addition, the measurement circuit 330 measures the orientation angle of the shaft 210 relative to the reference axis in real time (e.g., as a user tilts the shaft 210 to a desired orientation) and coordinates with the control circuit 350 to update the orientation angle communicated to a user (e.g., displayed on a display), almost instantaneously.

The measurement circuit 330 may include one or more sensors 510 and one or more transceivers 520. In one embodiment, the measurement circuit 330 uses signals from one or more sensors 510 to detect a change in orientation of a shaft 210. As the orientation of the shaft 210, the sensor 510 can detect this change and the measurement circuit 330 provides a measurement of the amount of change (in units of degrees) from the reference axis. In certain embodiments, the sensor 510 can be an accelerometer.

In certain embodiments, the measurement circuit 330 may use feedback from a first sensor 510 to determine a reference axis. For example, a first sensor 510 such as an accelerometer or gyroscope or other electronic, magnetic, and/or electromechanical sensor may determine a horizontal plane relative to an orientation of the surgical device 200. Based on the horizontal plane, the measurement circuit 330 may determine that the reference axis is perpendicular to the horizontal plane. The measurement circuit 330 may determine a horizontal plane determine the reference axis relative to the horizontal plane. For example, the horizontal plane may be a plane parallel to the ground or surface of an operating table and the reference axis may be perpendicular to the horizontal plane.

In certain embodiments, the measurement circuit 330 uses an orientation sensor 510. The orientation sensor 510 may determine a horizontal plane parallel to the ground and/or an orientation of the orientation sensor 510 relative to the horizontal plane. Such an orientation sensor 510 can be used by the measurement circuit 330 to determine the reference axis and/or one or more orientation sensors 510 may be used to determine an orientation of the surgical device 200 relative to the reference axis. One example of an orientation sensor 510 may be a mercury switch, such as a mercury tilt switch.

Alternatively, or in addition, the electronic circuit 400 may include a memory media 560. The memory media 560 is configured to store data representative of the reference axis. The measurement circuit 330 may retrieve data indicating the reference axis from the memory media 560. Data defining the reference axis may be stored in the memory media 560 during fabrication, during a calibration operation (a zeroing out operation), or at another time. The memory media 560 may be any of a variety of storage media and/or storage devices. In one embodiment, the memory media 560 is a non-volatile storage media. "Non-volatile storage media" refers to any hardware, device, component, element, or circuit configured to maintain an alterable physical characteristic used to represent a binary value of zero or one after a primary power source is removed. Non-volatile storage media may be used interchangeably herein with the term non-volatile memory media. In addition to storing data indicating a reference axis, the memory media 560 can store a variety of other data, including a set of desired/target orientation angles, a last measured orientation angle, measured linear distance, logic for operating or initializing the control circuit 350 and/or the like.

In certain embodiments, the electronic circuit 400 may be configured to enter a distance measuring mode. For example, in response to activation of a distance mode switch 260. In this mode, the measurement circuit 330 may serve to measure a linear distance. In certain embodiments, the measurement circuit 330 may include one or more transceivers 520. The one or more transceivers 520 of one surgical device 200 may send an electromagnetic wave pulse, magnetic wave pulse, or a light pulse to corresponding one or more transceivers of a second surgical device 200. The second surgical device 200 may be positioned at a point of origin and the surgical device 200 may be positioned at a destination point and the measurement circuit 330 may measure a linear distance between the two surgical devices based on characteristics of signals exchanged between the two surgical devices. The resulting linear measurement may be provided by the control circuit 350 to the output circuit 320 for communication to a user.

In certain embodiments, the calibration circuit 340 determines a reference axis 130. The calibration circuit 340 may include one or more sensors 530 to facilitate determining the reference axis 130. The sensor 530 may be a level sensor, tilt sensor, or another type of sensor. The sensor 530 can determine a horizontal plane and the calibration circuit 340 may determine a reference axis 130 based on that determined horizontal plane. The In certain embodiments, the calibration circuit 340 and/or measurement circuit 330 may utilize the same sensors (e.g., a common accelerometer). In another embodiment, the calibration circuit 340 and measurement circuit 330 may each use separate sensors 510, 530.

Figure 5:
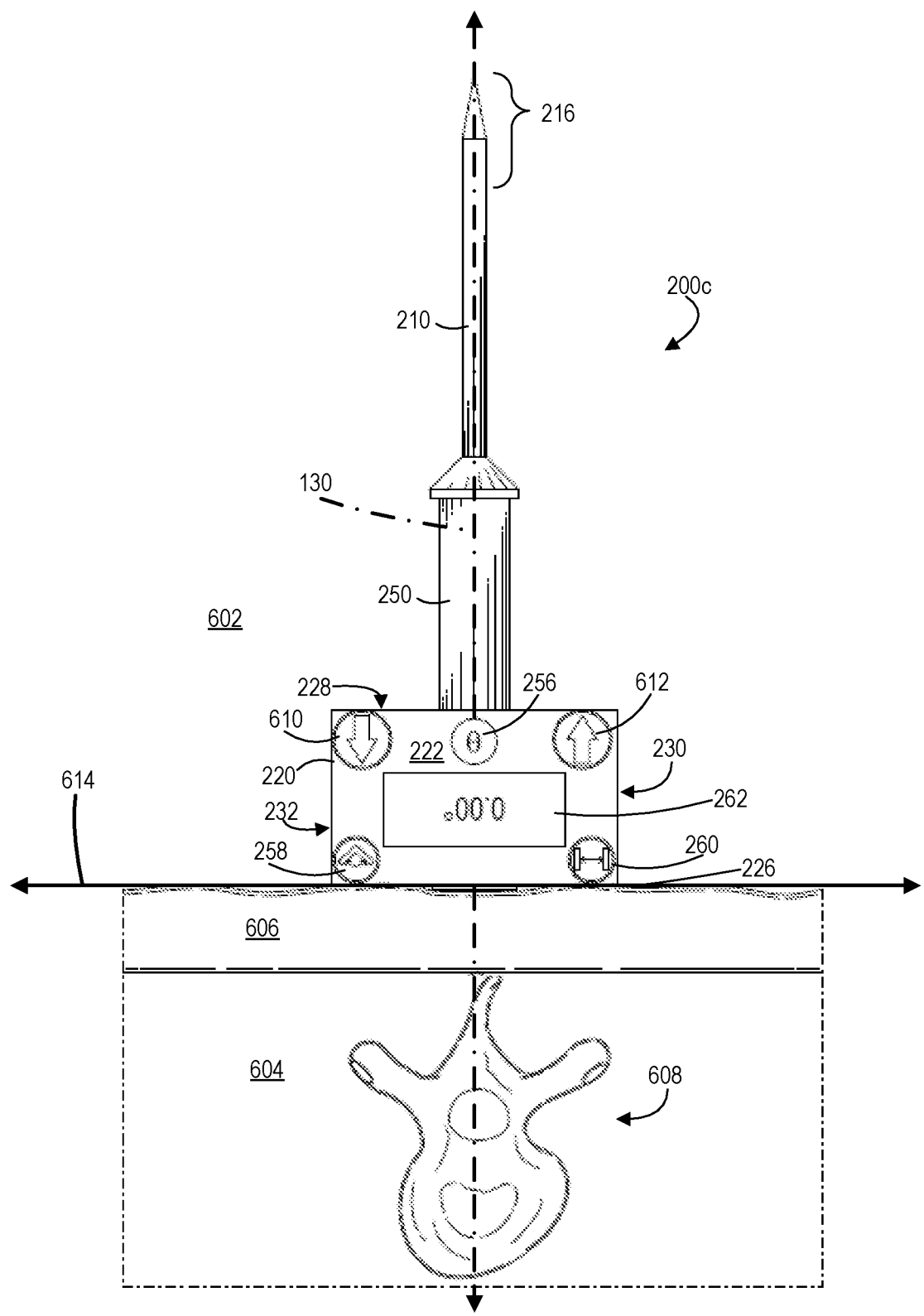
FIG. 5 is a perspective cut-away view of a surgical field and an intraoperative angle measurement apparatus according to one embodiment.

FIG. 5 is a perspective cut-away view of a surgical field and an intraoperative angle measurement apparatus according to one embodiment. FIG. 5 illustrates one example of a surgical device 200c and how the surgical device 200c can be used intraoperatively within a surgical field 602.

The surgical device 200c may have many structures, features, and functions, operations, and configuration similar or identical to those of the surgical device 200a or surgical device 200b described above, like parts are identified with the same reference numerals. Accordingly, the surgical device 200c may include a shaft 210, a housing 220, a head 240, a handle 250, and/or an electronic circuit 300/400 (within the housing 220).

In the illustrated embodiment, the surgical device 200c differs from the surgical device 200a or surgical device 200b because the surgical device 200c includes at least one surface of the housing 220 that is planar. In certain embodiments, one or more sensors (e.g., first sensor 510 and/or sensor 530) may be used by the electronic circuit 300/400 to determine a reference axis 130 and/or a horizontal plane from which a reference axis 130 can be determined. Alternatively, or in addition, the electronic circuit 300/400 can determine a reference axis 130 by retrieving data from memory media 560 that defines the reference axis 130.

In the illustrated embodiment, the surgical device 200c can use one of the planar surfaces of the housing 220 to determine a horizontal plane and/or reference axis 130. For example, the electronic circuit 300/400 can operate in a calibration mode to determine the horizontal plane and/or reference axis 130. The calibration mode can include placement of the housing 220 in a specific orientation, a known orientation, from which the electronic circuit 300/400 can determine the horizontal plane and/or reference axis 130 which in turn can be used to measure or determine orientation angles from either of the horizontal plane and/or reference axis 130. In one embodiment, the electronic circuit 300/400 may determine an orientation angle (e.g., angle A and/or angle B) based on a reference axis 130 perpendicular to a horizontal plane that parallel to a ML axis 122. The horizontal plane may be defined by one of the surfaces 222, 224, 226, 228, 230, 232 of the housing 220 during a calibration mode of the electronic circuit 300/400.

Now suppose, a surgical procedure, such as an orthopedic surgical procedure is to be performed on a patient. The patient may be positioned on an operating table in a prone position with the back of the patient facing upward. An area around, and/or including, the back of the patient may be prepared as a surgical field 602. FIG. 5 illustrates a cut-away view of the body 604, skin 606, and a vertebra 608 of the patient.

Now further suppose that a surgeon wants to use the surgical device 200c during the surgical procedure. The surgeon or an assistant may calibrate the surgical device 200c in preparation for use. Once calibrated, the surgical device 200c may rest within the surgical field 602 until needed.

In the illustrated embodiment, the surgical device 200c may include a planar anterior surface 222, a planar posterior surface 224 (not shown in FIG. 5), a planar superior surface 226, a planar inferior surface 228, a planar first lateral surface 230 and a planar second lateral surface 232. The anterior surface 222 may include a user interface 254. In another embodiment, the posterior surface 224 may also include a user interface 254 and a user interface 254 on either side may be used by a user. Alternatively, or in addition, a user interface 254 may be on one side and a separate display 262 may be on each side or the same display 262 may be visible from either side of the housing 220.

The user interface 254 may include a zero-out switch 256, an angle mode switch 258, a distance mode switch 260, a display 262, an up arrow button 610, and a down arrow button 612.

To calibrate the surgical device 200c, a user may press the zero-out switch 256 (for example, a button) (i.e., activate a zeroing switch). Pressing the zero-out switch 256 may send a zero-out input signal to a calibration circuit 340 of the electronic circuit 300/400. In response to the zero-out input signal, the calibration circuit 340 may determine a horizontal plane 614 and/or reference axis 130. In certain embodiments, re-orienting the surgical device 200c for the calibration mode may not be needed.

In the illustrated embodiment, the user may re-orient the surgical device 200c as part of the calibration process (calibration mode). After the zero-out switch 256 is activated or pressed a user may have some time (e.g., one to five seconds) to re-orient and/or position the surgical device 200c for the calibration circuit 340 to calibrate for orientation angle measurements.

In one embodiment, the user may re-orient and/or position the surgical device 200c for the calibration by resting the superior surface 226 of the housing 220 on the surface of the skin 606 of the patient in a position substantially centered above a patient's spine (e.g., one or more vertebrae 608). In this manner, the superior surface 226 (with the surgical device 200c positioned as shown in FIG. 5) serves to define, or serves as a suitable proxy to define, the horizontal plane 614 during a calibration mode. As explained above, the reference axis 130 can be defined as an axis perpendicular to the horizontal plane 614.

The user may position the surgical device 200c as shown in FIG. 5 before, after, or while pressing or activating the zero-out switch 256 which can send a zero-out input signal from the user. Of course, embodiments of the surgical device 200c can be configured to calibrate to identify the horizontal plane 614 and/or reference axis 130 using any one or more of the surfaces of the housing 220.

In one embodiment, the electronic circuit 300/400 may indicate that the surgical device 200c is calibrated by causing the display 262 to display 0 degrees, or flash 0 degrees, or provide another output signal indicating the calibration is completed. In certain embodiments, once the surgical device 200c is calibrated, the surgical device 200c may start measuring and reporting/displaying an orientation angle of the shaft 210 (surgical device 200c). Alternatively, or in addition, the surgical device 200c may not measure and report/display orientation angles until the user presses the angle mode switch 258 indicating that the user is prepared to use the surgical device 200c and obtain orientation angle readings.

Figure 6A:
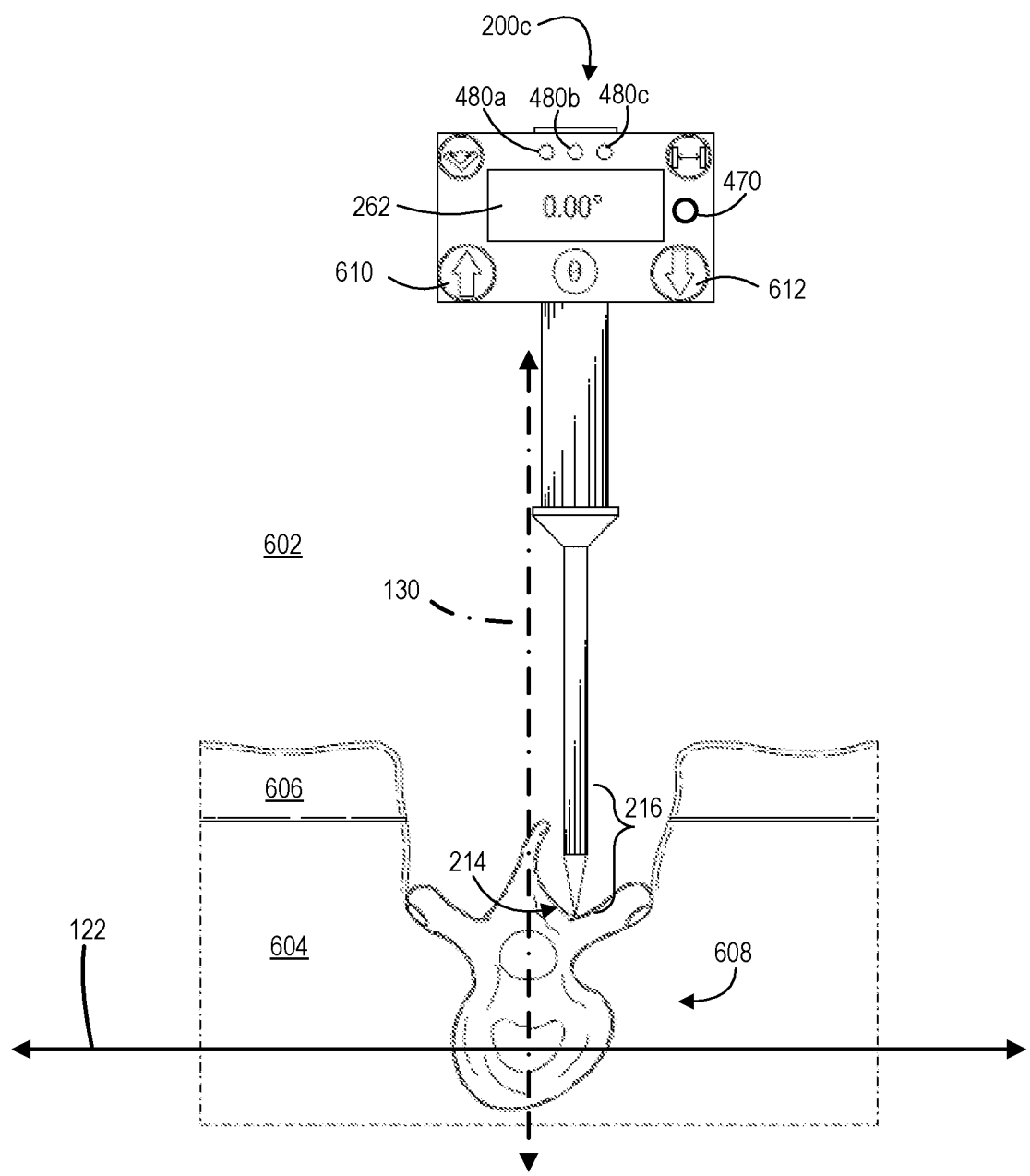
FIG. 6A is a perspective cut-away view of an intraoperative angle measurement apparatus in use in contact with a vertebra of a patient in a prone position in accordance with one embodiment.

FIG. 6A is a perspective cut-away view of an intraoperative angle measurement apparatus, surgical device 200c, in use to contact a vertebra of a patient in a prone position in accordance with one embodiment. Advantageously, the surgical device 200c can be a small handheld portable device that can accurately determine or confirm an orientation angle for using confirming a pedicle insertion trajectory on vertebrae of a patient.

The surgical device 200c may be used with a method for intraoperatively confirming a pedicle screw insertion trajectory on a vertebra of a patient. The method may start by positioning a patient on a table for a spinal surgery procedure such that a coronal plane of the patient is parallel to a floor supporting the table. Next, the surgical device 200c may be calibrated by positioning the surgical device 200c superficial to skin of the patient and substantially centering the surgical device 200c above the patient's spine. Next, the surgical device 200c may be calibrated to set a reference axis for the hand-held surgical device relative to the patient's spine. Next, a distal end 214 (e.g., bone probe 216) of the shaft 210 and/or surgical device 200c is placed on a surface of a pedicle of a vertebra of the patient's spine.

FIG. 6A illustrates a vertebra 608. A surgeon has created an opening that may expose one or more of the spinous process 104, first transverse process 106 and/or second transverse process 108. These processes 104, 106, 108, may be used as landmarks to identify the vertebra 608 and/or locate a surface point for the pedicle. Advantageously, the bone probe 216 can be placed on the surface point for the pedicle and the bone probe 216 remains in contact with the surface of the bone as an orientation angle is measured.

Figure 6B:
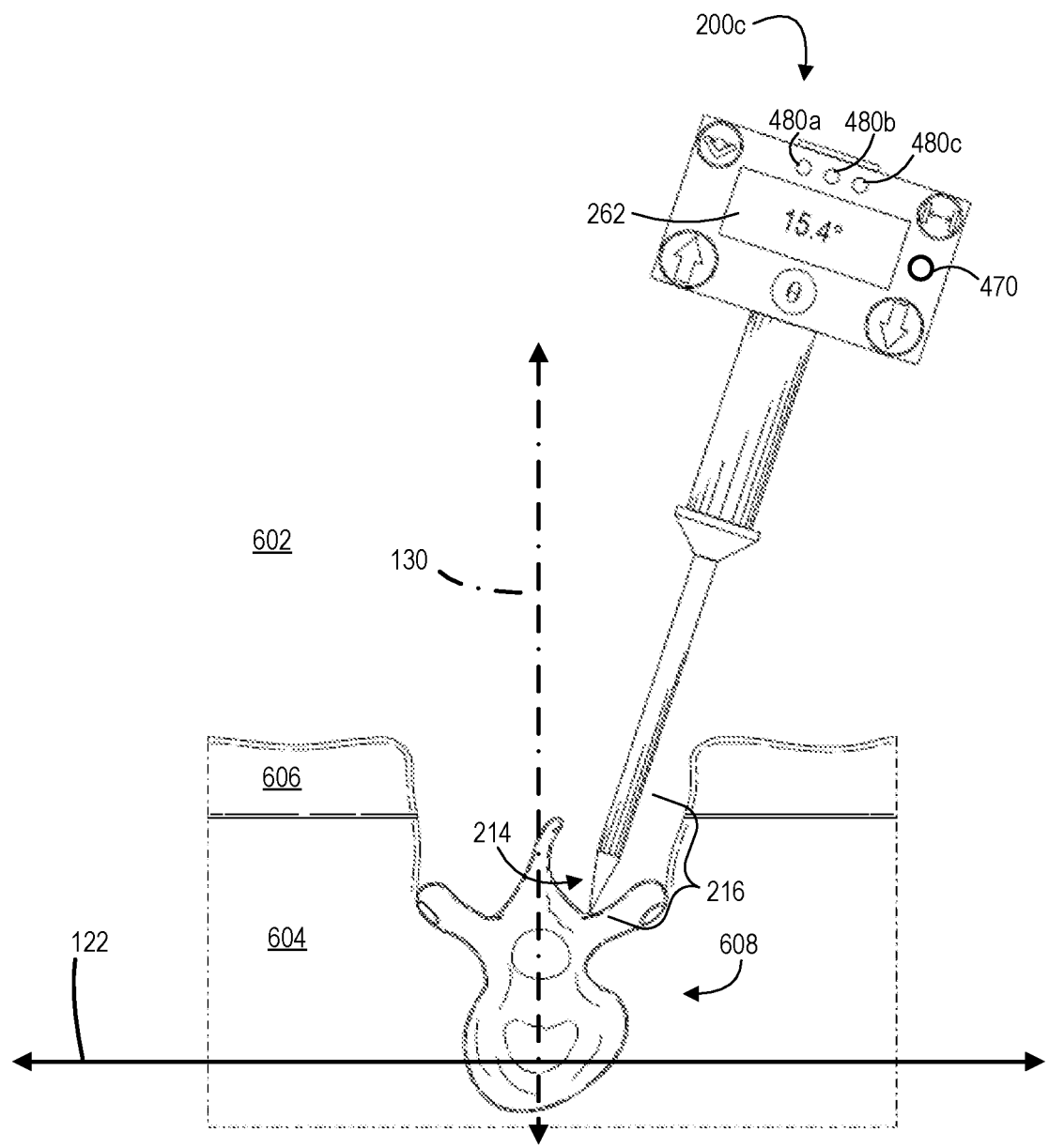
FIG. 6B is a perspective cut-away view of an intraoperative angle measurement apparatus in use.

Next, a user/surgeon may tilt the shaft 210/surgical device 200c to a desired orientation with the bone probe 216 remaining in stationary contact with cortical bone of the pedicle of the vertebrae. FIG. 6B is a perspective cut-away view after a surgeon has tilted the shaft 210/surgical device 200c to a desired orientation. The display 262 shows the current orientation of angle. Suppose the right pedicle of the vertebra 608 is at 15.4 degrees. If this is the case, then the surgical device 200c shows the insertion trajectory needed to deploy fixation devices into the pedicle.

At this stage, a surgeon may employ a variety of techniques to mark or preserve or denote the insertion trajectory. For example, the surgeon may strike the head of the surgical device 200c (with a hand, a hammer, and/or a mallet) to cause the bone probe 216 to penetrate the cortical surface of the vertebra 608. Or, the surgeon may press the surgical device 200c towards the vertebra 608 and cause the bone probe 216 to form a pilot hole in the pedicle. The pilot hole may then be used with other instruments (such as an electronic pedicle probe, or manual pedicle probe) to confirm the position of the pilot hole in the pedicle. The pilot hole may be tapped for a subsequent pedicle screw. In certain embodiments, a surgeon may press a pedicle probe through the pilot hole and into cancellous bone of the vertebra 608 to prepare the pedicle for a pedicle screw.

The electronic circuit 300/400 may measure an orientation of the shaft in relation to the reference axis with the shaft in the desired orientation. The electronic circuit 300/400 may also determine an orientation angle of the shaft relative to the reference axis with the shaft in the desired location. The electronic circuit 300/400 may communicate the orientation angle to a user/surgeon. For example, the electronic circuit 300/400 may display the determined orientation angle using the display 262. The user/surgeon may confirm that the orientation angle satisfies a target insertion trajectory previously determined by a surgeon conducting the spinal surgery procedure. Then, a surgeon may proceed with one or more steps of the spinal surgery procedure.

In certain embodiments, the surgical device 200c may be configured to assist a surgeon in performing these one or more steps of the spinal surgery procedure. In one embodiment, the surgeon may align another instrument such as an awl, bone probe, surgical drill bit, of the like, with the surgical device 200c. In this manner, the instrument used has the target insertion trajectory. In another embodiment, the surgical device 200c and/or electronic circuit 300/400 may be coupled to another instrument such that tilting that instrument will indicate a current orientation angle.

Referring now to FIGS. 6A, 6B, in another embodiment, a user may input a desired or target orientation angle before or after placing the bone probe 216 on the cortical bone. The desired or target orientation angle may be input by activating the respective up arrow button 610 and/or down arrow button 612 until the display 262 shows the desired or target orientation angle. The electronic circuit 300/400 may store the desired or target orientation angle in memory media 560.

In the illustrated embodiment, the surgical device 200c may include one or more lights 480a, b, c and/or a speaker 470 as part of the user interface 254. The lights 480 may emit white or colored light of the same or different colors. The lights 480 may flash or blink. The speakers 470 may emit different sounds and/or tones of one or more frequencies and/or may do so at different frequencies.

In one embodiment, the surgical device 200c may use the lights 480a, b, c and/or speakers 470 to communicate when the orientation of the surgical device 200c is closer to, further away from or at the desired or target orientation angle. Those of skill in the art will appreciate a variety of ways, patterns, and/or configurations for how the electronic circuit 300/400 may activate the lights 480 and/or speakers 470 and/or haptic feedback devices 490 to convey how a current orientation angle relates to a desired or target orientation angle.

In one embodiment, the light 480a may be configured to illuminate when the orientation angle of the surgical device 200c is outside a range of desired orientation angles. For example, the light 480a may illuminate red when the orientation angle of the surgical device 200c is outside a range of desired orientation angles. The range of angles may be measured in hundredths or tenths of degrees or degrees and may span a range of between 1 and 10 degrees.

The light 480b may be configured to illuminate when the orientation angle of the surgical device 200c is inside a range of desired orientation angles. The range of desired orientation angles for the light 480b may be the same or different from the range of desired orientation angles for the light 480a. In one example, the light 480b may illuminate orange or yellow when the orientation angle of the surgical device 200c is inside a range of desired orientation angles.

The light 480c may be configured to illuminate when the orientation angle of the surgical device 200c is substantially at a desired orientation angle. In one example, the light 480c may illuminate green when the orientation angle of the surgical device 200c is substantially at a desired orientation angle. In another embodiment, each of the lights 480 may illuminate the same color or flash or blink to indicate where a current orientation angle is relative to the desired or target orientation angle.

Those of skill in the art will appreciate that as with the lights 480, the electronic circuit 300/400 may activate one or more speakers 470 with different sounds (e.g., beeps, blips, etc.) that indicate where a current orientation angle is relative to the desired or target orientation angle.

FIGS. 7A-7E illustrate perspective views of different embodiments of a bone probe that can be used with an intraoperative angle measurement apparatus in accordance with one embodiment. FIGS. 7A-7E illustrate different examples, those of skill in the art will appreciate that other variations of the bone probe 216 may be used with embodiments of the present disclosure and within the scope of the claims below.

Figure 7A:
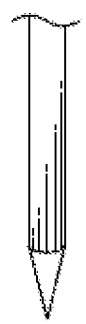
FIGS. 7A-7E illustrate perspective views of different embodiments of a bone probe that can be used with an intraoperative angle measurement apparatus in accordance with different embodiments.

FIG. 7A illustrates a bone probe 216 having a distal end that comes to a sharp point and is connected to, and/or formed with, the shaft 210. The sharp point facilitates the bone probe 216 remaining in contact with the cortical bone as an orientation angle is determined.

Figure 7B:
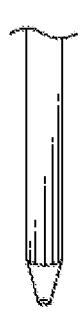

FIG. 7B illustrates a bone probe 216 having a distal end that includes a coaxial opening that extends from a distal end of the bone probe 216 to a proximal end. The coaxial opening may connect to an opening in, or be a same opening as, one in a shaft 210 such that the shaft 210 is cannulated. The coaxial opening may have a diameter that accepts passage of a variety of instruments that a surgeon may use as part of a procedure to deploy a fixation device (e.g., a pedicle screw). The coaxial opening may also facilitate the bone probe 216 remaining in contact with the cortical bone as an orientation angle is determined.

Figure 7C:
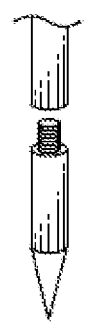

FIG. 7C illustrates a bone probe 216 having a distal end that comes to a sharp point and proximal end that includes threads that connect the bone probe 216 to a shaft 210. The threads on one or the other of the bone probe 216 and the shaft 210 may be corresponding internal and external threads.

Figure 7D:
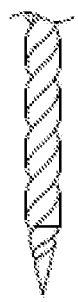

FIG. 7D illustrates a bone probe 216 having a distal end that comes to a sharp point and is connected to and/or formed with the shaft 210. The bone probe 216 may include a plurality of threads or flutes on the external surface of the bone probe 216. The threads or flutes can be configured to cut into bone such that rotation of the bone probe 216 can cause the bone probe 216 to drill down through the cortical surface and into the bone. In this manner, a surgeon may rotate the bone probe 216 either manually, or with a powered driver, to penetrate the cortical bone at a trajectory angle provided by the surgical device 200c.

Figure 7E:

FIG. 7E illustrates a bone probe 216 having a distal end that includes a coaxial opening that extends from a distal end of the bone probe 216 to a proximal end. The coaxial opening may connect to an opening in, or be a same opening as, one in a shaft 210 such that the shaft 210 is cannulated. The bone probe 216 may include a plurality of threads or flutes on the external surface of the bone probe 216. The threads or flutes can be configured to cut into bone such that rotation of the bone probe 216 can cause the bone probe 216 to drill down through the cortical surface and into the bone.

In this manner, a surgeon may rotate the bone probe 216 either manually or with a powered driver to penetrate the cortical bone at a trajectory angle provided by the surgical device 200c. Alternatively, or in addition, the coaxial opening may have a diameter that accepts passage of a variety of instruments that a surgeon may use as part of a procedure to deploy a fixation device (e.g., a pedicle screw). A surgeon may use the coaxial opening to insert a drill bit or a probe or other instrument into the bone probe 216 to deploy a fixation device.

In certain embodiments, the bone probe 216 of FIG. 7E may be a modular bone probe 216 such as the one illustrated in FIG. 7C that connects to a shaft 210. In one embodiment, the bone probe 216 is modular and is a cannulated drill bit. In another embodiment, the bone probe 216 (in any of the illustrated embodiments) is modular and planar and tapers to a point, for example such as with the distal end of an osteotome tip.

FIG. 8A illustrates a bone probe 216 having a distal end that comes to a sharp point and is connected to and/or formed with the shaft 210. The sharp point facilitates the bone probe 216 remaining in contact with the cortical bone as an orientation angle is determined. The bone probe 216 may include a plurality of tap threads on the external surface of the bone probe 216. The tap threads can be configured to cut internal threads into a preformed opening in bone such that rotation of the bone probe 216 can form internal threads in the bone. Alternatively, or in addition, the tap threads can be configured to cut internal threads and also form an opening in bone such that rotation of the bone probe 216 can form internal threads in a passage in the bone. In this manner, a surgeon may rotate the bone probe 216 either manually or with a powered driver to form internal threads for a fixation device, such as a pedicle screw.

FIG. 8B illustrates a bone probe 216 having a distal end that includes a coaxial opening that extends from a distal end of the bone probe 216 to a proximal end. The coaxial opening may connect to an opening in, or be a same opening as one in, a shaft 210 such that the shaft 210 is cannulated. The coaxial opening may have a diameter that accepts passage of a variety of instruments that a surgeon may use as part of a procedure to deploy a fixation device (e.g., a pedicle screw). The coaxial opening may also facilitate the bone probe 216 remaining in contact with the cortical bone as an orientation angle is determined.

The bone probe 216 may include a plurality of tap threads on the external surface of the bone probe 216. The tap threads can be configured to cut internal threads into bone such that rotation of the bone probe 216 can form internal threads in the bone. In this manner, a surgeon may rotate the bone probe 216 either manually or with a powered driver to form internal threads for a fixation device, such as a pedicle screw.

FIG. 8C illustrates a bone probe 216 having a distal end that comes to a sharp point and proximal end that includes threads that connect the bone probe 216 to a shaft 210. The threads on one or the other of the bone probe 216 and the shaft 210 may be corresponding internal and external threads. In the illustrated embodiment, the bone probe 216 may be modular and can be connected to the shaft 210. The bone probe 216 may include a plurality of tap threads on the external surface of the bone probe 216. The tap threads can be configured to cut internal threads into bone such that rotation of the bone probe 216 can form internal threads in the bone. In this manner, a surgeon may rotate the bone probe 216 either manually or with a powered driver to form internal threads for a fixation device, such as a pedicle screw.

FIG. 8D illustrates a bone probe 216 having a distal end that comes to a flat sharp point, like a chisel, and is connected to, and/or formed with, the shaft 210. The flat sharp point facilitates the bone probe 216 remaining in contact with the cortical bone as an orientation angle is determined.

FIG. 8E illustrates a bone probe 216 having a distal end that comes to a flat sharp point, like a chisel, and proximal end that includes threads that connect the bone probe 216 to a shaft 210. The threads on one or the other of the bone probe 216 and the shaft 210 may be corresponding internal and external threads. The corresponding internal and external threads enable the bone probe 216 to be modular and be connected to the shaft 210 or removed, as needed.

Those of skill in the art will appreciate that the bone probe 216 may include any combination of the features illustrated and described in relation to FIGS. 7A-7E and 8A-8E.

Those of skill in the art will appreciate that certain one or more of the components of the surgical device 200a, b, c can be used together or separately in connection with other surgical instruments and come within the scope of the claims of the present disclosure. For example, the housing 220, electronic circuit 300/40, and power supply 360 can be used in a single unit and connected or coupled with another instrument in order use take advantage of the features and functions of the present disclosure with that other instrument.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles set forth herein.

While specific embodiments and applications of the present disclosure have been illustrated and described, it is to be understood that the scope of this disclosure is not limited to the precise configuration and components disclosed herein. Various modifications, changes, and variations which will be apparent to those skilled in the art may be made in the arrangement, operation, and details of the methods and systems of the present disclosure set forth herein without departing from it spirit and scope.

It should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects can be present in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Those of skill in the art will appreciate that the solutions provided in present disclosure may be accomplished with all, or less than all, of the components, structures, features, or aspects disclosed in the specification or illustrated in the figures in relation or a particular embodiment or claim.

What is claimed is:

1. A surgical device for intraoperative angle measurements during surgery on a patient, the surgical device comprising:
    a shaft comprising:
        a proximal end; and
        a distal end comprising a bone probe comprising a tapered tip configured to engage and remain in contact with cortical bone of the patient while a user orients the shaft to a desired orientation; and
    a housing coupled to the shaft, the housing comprising:
        an electronic circuit configured to measure an orientation angle, the electronic circuit comprising:
            an input device configured to receive user input data;
            a measurement circuit configured to measure a change in orientation of the shaft in relation to a reference axis;
            a control circuit coupled to the input device and measurement circuit and configured to determine the orientation angle of the shaft relative to the reference axis;
            an output device coupled to the control circuit and configured to communicate the orientation angle to the user; and
        a power supply configured to provide power to the electronic circuit.

2. The surgical device of claim 1, comprising a calibration circuit configured to determine the reference axis for the electronic circuit, the reference axis being perpendicular to a horizontal plane of a surgical field.

3. The surgical device of claim 2, wherein the housing comprises a planar surface and the electronic circuit determines the horizontal plane based on the planar surface resting on skin of the patient and substantially centered above a patient's spine of a patient in a prone position and based on a zero-out input signal from a user.

4. The surgical device of claim 2, wherein the calibration circuit determines the reference axis in response to a zero-out input signal from a user.

5. The surgical device of claim 1, wherein the electronic circuit comprises a sensor configured to determine a horizontal plane and the electronic circuit determines the reference axis relative to the horizontal plane.

6. The surgical device of claim 1, comprising a linear measurement circuit configured to measure a linear distance between the surgical device and a second surgical device.

7. The surgical device of claim 1, wherein the output device comprises an audio output device configured to provide one or more audio signals that communicate the orientation angle.

8. The surgical device of claim 1, comprising non-volatile storage media configured to store data for the reference axis and wherein the electronic circuit determines the reference axis based on the data for the reference axis.

9. The surgical device of claim 1, wherein the measurement circuit comprises a sensor configured to detect a change in orientation of the shaft.

10. The surgical device of claim 1, wherein the measurement circuit is configured to measure an orientation of the shaft in response to user input data.

11. The surgical device of claim 1, wherein the measurement circuit is configured to measure an orientation of the shaft as a user tilts the shaft to a desired orientation.

12. The surgical device of claim 1, wherein the shaft comprises a head near the proximal end, the head configured to receive a strike and the bone probe is configured to penetrate cortical bone in response to the strike.

13. The surgical device of claim 1, wherein the shaft is cannulated from the proximal end to the distal end and configured to accept one or more of a K-wire, a bone bore, an awl, a pedicle probe, a pedicle implant, and a pedicle inserter.

14. A surgical device for intraoperative angle measurements during surgery on a patient, the surgical device comprising:
  a shaft comprising:
    a proximal end; and
    a distal end opposite the proximal end, the distal end configured to contact cortical bone of a patient; and
  an electronic circuit coupled to the shaft, the electronic circuit configured to measure an orientation angle, the electronic circuit comprising:
    a zero-out switch configured to convey a zero-out signal;
    a calibration circuit configured to determine a reference axis for the electronic circuit in response to the zero-out signal, wherein the calibration circuit is further configured to receive input from one or more sensors;
    a measurement circuit configured to measure an orientation of the shaft in relation to the reference axis as a user tilts the shaft to a desired orientation, the measurement circuit comprising an orientation sensor;
    a control circuit coupled to the zero-out switch, calibration circuit, and measurement circuit and configured to determine an orientation angle of the shaft relative to the reference axis;
    a display device coupled to the control circuit and configured to display the orientation angle to a user; and
    a power supply configured to provide electric current to the electronic circuit.

15. The surgical device of claim 14, comprising:
  a housing that comprises the electronic circuit and the power supply;
  a handle closer to the proximal end of the shaft;
  a bone probe at the distal end of the shaft;
  a head at the proximal end of the shaft, the head configured to accept a driving force to form a pedicle screw pilot hole in a vertebra of the patient;
  an angle mode switch configured to change an operating mode of the electronic circuit from measuring distance to measuring the orientation angle of the shaft; and
  a distance mode switch configured to change an operating mode of the electronic circuit from measuring the orientation angle of the shaft to measuring a distance between the surgical device and a second surgical device.

16. The surgical device of claim 15, wherein the power supply, electronic circuit, housing, handle, head, and shaft are configured for single use with one patient.

17. The surgical device of claim 16, wherein the orientation angle displayed to a user is accurate to within three tenths of a degree.

18. A surgical device for intraoperative angle measurements during surgery on a patient, the surgical device comprising:
  a shaft comprising:
    a proximal end;
    a distal end opposite the proximal end; and
    a bone probe coupled to the shaft at the distal end, the bone probe configured to engage, penetrate into, and remain in stationary contact with cortical bone of the patient while a user orients the shaft to a desired orientation;
  a housing coupled to the shaft near the proximal end, the housing comprising:
    an anterior surface, a posterior surface, a superior surface, an inferior surface, and a pair of opposite lateral surfaces;
    a user interface configured to receive input data from a user by way of a zeroing switch and to display output data to a user on a display device;
    an electronic circuit configured to determine an orientation angle based on a reference axis perpendicular a horizontal plane defined by one of the surfaces of the housing during a calibration mode of the electronic circuit; and
    a power supply configured to provide power to the electronic circuit;
  a handle coaxial with the shaft and positioned between the bone probe and the proximal end of the shaft; and
  a head coupled to the shaft near the proximal end, the head configured to receive an axial force along the shaft from a user when the shaft is oriented at the orientation angle.

19. The surgical device of claim 18, wherein the electronic circuit enters the calibration mode in response to activation of the zeroing switch.

20. The surgical device of claim 18, wherein the user interface comprises:
  a first light configured to indicate that the orientation angle is outside a range of desired orientation angles;
  a second first light configured to indicate that the orientation angle is within a range of desired orientation angles; and
  a third light configured to indicate that the orientation angle substantially at the desired orientation angle.

21. A surgical device for intraoperative angle measurements during surgery on a patient, the surgical device comprising:
  a shaft comprising:
    a proximal end; and a distal end comprising a bone probe configured to engage and remain in contact with cortical bone of the patient while a user orients the shaft to a desired orientation; and a housing coupled to the shaft, the housing comprising:
an electronic circuit configured to measure an orientation angle, the electronic circuit comprising:
an input device configured to receive user input data;
a measurement circuit configured to measure a change in orientation of the shaft in relation to a reference axis;
a control circuit coupled to the input device and measurement circuit and configured to determine the orientation angle of the shaft relative to the reference axis;
an output device coupled to the control circuit and configured to communicate the orientation angle to the user; and
a power supply configured to provide power to the electronic circuit; and a handle, wider than the shaft, positioned between the distal end and the housing.

22. The surgical device of claim 21, wherein the shaft is cannulated from the proximal end to the distal end and configured to accept one or more of a K-wire, a bone bore, an awl, a pedicle probe, a pedicle implant, and a pedicle inserter.

23. The surgical device of claim 21, wherein the shaft comprises a head near the proximal end, the head configured to receive a strike and the bone probe is configured to penetrate cortical bone in response to the strike.

* * * * *